United States Patent
Enderling et al.

(10) Patent No.: US 10,783,628 B2
(45) Date of Patent: Sep. 22, 2020

(54) RADIOTHERAPY TARGETED TO PROMOTE A SYSTEMIC ABSCOPAL EFFECT

(71) Applicant: H. LEE MOFFITT CANCER CENTER AND RESEARCH INSTITUTE, INC., Tampa, FL (US)

(72) Inventors: Heiko Enderling, Tampa, FL (US); Jan T. Poleszczuk, Tampma, FL (US); Kimberly A. Luddy, Odessa, FL (US); Eduardo G. Moros, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 71 days.

(21) Appl. No.: 16/000,673

(22) Filed: Jun. 5, 2018

(65) Prior Publication Data
US 2019/0114765 A1     Apr. 18, 2019

Related U.S. Application Data

(63) Continuation of application No. 15/301,793, filed as application No. PCT/US2015/024278 on Apr. 3, 2015, now Pat. No. 9,990,715.

(Continued)

(51) Int. Cl.
| | |
|---|---|
| *H04N 7/18* | (2006.01) |
| *G06T 7/00* | (2017.01) |
| *G06T 19/00* | (2011.01) |
| *G16Z 99/00* | (2019.01) |
| *G16H 20/40* | (2018.01) |
| *G16H 30/20* | (2018.01) |

(Continued)

(52) U.S. Cl.
CPC ............ *G06T 7/0012* (2013.01); *A61B 5/055* (2013.01); *A61B 6/032* (2013.01); *A61B 6/037* (2013.01); *A61B 18/12* (2013.01); *A61B 18/1815* (2013.01); *A61N 5/1039* (2013.01); *A61N 5/1084* (2013.01); *A61N 7/02* (2013.01); *G06F 19/00* (2013.01); *G06F 19/321* (2013.01); *G06F 19/3481* (2013.01); *G06T 19/00* (2013.01); *G16H 20/40* (2018.01); *G16H 30/20* (2018.01); *G16H 50/20* (2018.01); *G16H 50/30* (2018.01); *G16Z 99/00* (2019.02); *A61B 2018/00577* (2013.01); *A61B 2034/107* (2016.02); *G06T 2207/30096* (2013.01); *G06T 2207/30104* (2013.01); *G16H 50/50* (2018.01)

(58) Field of Classification Search
CPC .................................................. G06T 7/0012
USPC ....................................................... 382/131
See application file for complete search history.

(56) References Cited

U.S. PATENT DOCUMENTS

| | | |
|---|---|---|
| 2006/0034767 A1 | 2/2006 | Lum et al. |
| 2009/0123428 A1 | 5/2009 | Hall et al. |
| 2009/0274352 A1 | 11/2009 | Chang et al. |

FOREIGN PATENT DOCUMENTS

WO     2014052707 A2     4/2014

OTHER PUBLICATIONS

International Search Report and Written Opinion issued for International Application No. PCT/US15/24278, dated Jul. 10, 2015.

(Continued)

*Primary Examiner* — Stephen P Coleman
(74) *Attorney, Agent, or Firm* — Meunier Carlin & Cufman LLC

(57) ABSTRACT

Methods for personalized treatment of tumor lesions in subject with metastatic cancer are disclosed.

12 Claims, 23 Drawing Sheets

Related U.S. Application Data

(60) Provisional application No. 61/975,573, filed on Apr. 4, 2014.

(51) Int. Cl.

| | | |
|---|---|---|
| *G16H 50/30* | (2018.01) | |
| *G16H 50/20* | (2018.01) | |
| *A61B 5/055* | (2006.01) | |
| *A61B 6/03* | (2006.01) | |
| *A61B 18/12* | (2006.01) | |
| *A61B 18/18* | (2006.01) | |
| *A61N 5/10* | (2006.01) | |
| *A61N 7/02* | (2006.01) | |
| *G06F 19/00* | (2018.01) | |
| *G16H 50/50* | (2018.01) | |
| *A61B 34/10* | (2016.01) | |
| *A61B 18/00* | (2006.01) | |

(56) References Cited

OTHER PUBLICATIONS

International Preliminary Report on Patentability issued for International Application No. PCT/US15/24278, dated Oct. 13, 2016.
Zitvogel L, et al. Nat Rev Immunol. 2008 8(1):59-73.
Couzin-Frankel J. Science. 2013 342(6165):1432-3.
Reits EA, et al. J Exp Med. 2006 203(5):1259-71.
Lugade AA, et al. J Immunol. 2005 174(12):7516-23.
Vatner RE, et al. Front Oncol. 2014 4:325.
Demaria S, et al. Int J Radiat Oncol Biol Phys. 2004 58(3):862-70.
Antoniades J, et al. Int J Radiat Oncol Biol Phys. 1977 2(1-2):141-7.
Wersall PJ, et al. Acta Oncol. 2006 45(4):493-7.
Ehlers G, et al. Br J Radiol. 1973 46(543):220-2.
Kaminski JM, et al. Cancer Treat Rev. 2005 31(3):159-72.
Akutsu Y, et al. Int J Oncol. 2007 31(3):509-15.
Kuznetsov VA, et al. Bull Math Biol. 1994 56(2):295-321.
Wilkie KP. Adv Exp Med Biol. 2013 734:201-34.
d'Onofrio A, et al. Phys Rev E Stat Nonlin Soft Matter Phys. 2011 84(3 Pt 1):031910.
Arciero JC, et al. Discret Contin Dyn S. 2004 4(1):39-58.
Kirchner D, et al. J Math Biol. 1998 37(3):235-52.
Kronik N, et al. PloS one. 2010 5(12):e15482.
Kronik N, et al. Cancer Immunol Immunother. 2008 57(3):425-39.
Cappuccio A, et al. Cancer Res. 2006 66(14):7293-300.
Daisne JF, et al. Radiother Oncol. 2003 (69): 247-150.
Mikhak Z, et al. J Exp Med. 2013 210(9):1855-69.
Calzascia T, et al. Immunity. 2005 22(2):175-84.
Valentin J. Annals of the ICRP. 2002 32(3-4):1-277.
Abduljalil K, et al. Clin Pharmacokinet. 2012 51(6):365-96.
Puskas Z, et al. Der Radiologe. 1996 36(9):750-7.
McGuire A, et al. Cancer Metastasis Rev. 2015 34(1):145-55.
Kuznetsov VA, et al. Math Comput Model. 2001 33(12-13):1275-87.
Tufail S, et al. Front Immunol. 4:254, 2013.
Marte B. Nature. 501(7467):327, 2013.
Ye J, et al. Cancer Res. 73(20):6137-48, 2013.
Ward ST, et al. The Lancet. 381:S113, 2013.
Demaria S, et al. Clin Cancer Res. 11(2 Pt 1):728-34, 2005.
Hiniker SM, et al. N Engl J Med. 366(21):2035-6, 2012.
Finkelstein SE, et al. Immunotherapy. 4(4):373-382, 2012.
Galon J, et al. J Transl Med. 10:1, 2012.
Sharma A, et al. Clin Cancer Res. 19(17):4843-53, 2013.
Seung SK, et al. Sci Transl Med. 4(137):137ra74, 2012.
Postow MA, et al. N Engl J Med. 366(10):925-31, 2012.
Ohba K, et al. Gut. 43(4):575-7, 1998.

$$T_N = T_N(1-T) - (h_1 + X_f(t))T_N + h_2 T_I$$
$$- X_T(t)T_N$$

$$T_I = T_I(1-T) - h_3 T_I E + (h_1 + X_f(t))T_N$$
$$- h_2 T_I - X_T(t)T_I$$

$$E = h_4 T_I + [Y(t) - h_5 - X_E(t)]E$$

$$R = h_6 T - [h_6 + X_R(t)]R$$

In lymph node $i$:

$$\underbrace{\dot{C}_i}_{\substack{\text{immune}\\\text{signal}\\\text{in lymph}\\\text{node } i}} = \underbrace{\sum_{e_i} f_{i,e_i}}_{\substack{\text{cytokine flux}\\\text{to nearby}\\\text{lymph nodes}}} + \underbrace{f_{i,j}}_{\substack{\text{cytokine flux}\\\text{to metastatic}\\\text{site}}} - \underbrace{\gamma C_i}_{\substack{\text{cytokine}\\\text{decay}}}$$

In metastasis $j$:

$$\underbrace{\dot{C}_j}_{\substack{\text{immune}\\\text{signal}\\\text{in met } j}} = \underbrace{-\gamma C_j}_{\substack{\text{cytokine}\\\text{decay}}} - \underbrace{f_{j,i}}_{\substack{\text{lymph}\\\text{flux}}} + \underbrace{Y(t)}_{\substack{\text{immuno-}\\\text{therapy}}} + \underbrace{\sum_\ell aT_j\left(t_\ell^{\text{rad}}\right)e^{-\eta\left(t-t_\ell^{\text{rad}}\right)} \cdot \mathbf{1}_{(t_\ell^{\text{rad}},\infty)}(t)}_{\text{increased immunogenicity from radiation}}$$

$$\underbrace{\dot{T}_j}_{\substack{\text{size of}\\\text{met } j}} = \underbrace{\alpha_1 T_j\left(1-\frac{T_j}{K}\right)}_{\text{tumor growth}} - \underbrace{\gamma \frac{T_j}{1+T_j/E_j}}_{\substack{\text{tumor death}\\\text{from immune}}} - \underbrace{X_T(t)T_j}_{\substack{\text{radiation}\\\text{death}}}$$

$$\underbrace{\dot{E}_j}_{\substack{\text{immune}\\\text{cells in}\\\text{met } j}} = \underbrace{\delta T_j(1+sC_j)}_{\text{immune activation}} - \underbrace{\mu E_j}_{\substack{\text{immune}\\\text{death}}} - \underbrace{X_E(t)E_j}_{\substack{\text{radiation}\\\text{death}}}$$

with:

$$\underbrace{f_{m,n}}_{\substack{\text{lymph-metastatic}\\\text{flux}}} = \underbrace{k|C_m-C_n|e^{-\lambda L_{mn}} \cdot \mathbf{1}_{(-\infty,0)}(C_m-C_n)}_{\text{flux from node } n \text{ to node } m} - \underbrace{k|C_m-C_n| \cdot \mathbf{1}_{(0,\infty)}(C_m-C_n)}_{\text{flux from node } m \text{ to node } n}$$

FIG. 9

$$\underbrace{\dot{\tilde{T}}_N}_{\substack{\text{tolerogenic}\\\text{T cells}}} = \underbrace{\tilde{T}_N\left(1-\tilde{T}\right)}_{\text{tumor growth}} - \underbrace{\left(h_1 + \tilde{X}_f(t)\right)\tilde{T}_N + h_2\tilde{T}_I}_{\text{immunogenicity transition}} - \underbrace{\tilde{X}_T(t)\tilde{T}_N}_{\substack{\text{radiation}\\\text{death}}}$$

$$\underbrace{\dot{\tilde{T}}_I}_{\substack{\text{immunogenic}\\\text{T cells}}} = \underbrace{\tilde{T}_I\left(1-\tilde{T}\right)}_{\text{tumor growth}} - \underbrace{h_3\tilde{T}_I\tilde{E}}_{\substack{\text{immune}\\\text{killing}}} + \underbrace{\left(h_1 + \tilde{X}_f(t)\right)\tilde{T}_N - h_2\tilde{T}_I}_{\text{immunogenicity transition}} - \underbrace{\tilde{X}_T(t)\tilde{T}_I}_{\substack{\text{radiation}\\\text{death}}}$$

$$\underbrace{\dot{\tilde{E}}}_{\substack{\text{effector}\\\text{T cells}}} = \underbrace{h_4\tilde{T}_I}_{\substack{\text{immune}\\\text{response}}} + [\underbrace{\tilde{Y}(t)}_{\substack{\text{immuno-}\\\text{therapy}}} - \underbrace{h_4\tilde{R}}_{\substack{\text{Treg}\\\text{suppression}}} - \underbrace{h_5}_{\substack{\text{death}\\\text{rate}}} - \underbrace{\tilde{X}_E(t)}_{\substack{\text{radiation}\\\text{death}}}]\tilde{E}$$

$$\underbrace{\dot{\tilde{R}}}_{\text{Tregs}} = \underbrace{h_6\tilde{T}}_{\substack{\text{immune}\\\text{response}}} - [\underbrace{h_6}_{\substack{\text{death}\\\text{rate}}} + \underbrace{\tilde{X}_R(t)}_{\substack{\text{radiation}\\\text{death}}}]\tilde{R}$$

FIG. 11

RADIOTHERAPY TARGETED TO PROMOTE A SYSTEMIC ABSCOPAL EFFECT

CROSS-REFERENCE TO RELATED APPLICATIONS

This application claims benefit of U.S. Provisional Application No. 61/975,573 filed Apr. 4, 2014, which is hereby incorporated herein by reference in its entirety.

BACKGROUND

Cancer is a heterogeneous group of malignant diseases that, in 2012, were responsible for more than 14% of deaths worldwide. Despite decades of effort, most cancers remain incurable, which is largely due the step change from localized to metastatic disease. Transformed cancer cells are confronted with an innate and adaptive immune surveillance, and it is believed that tumors that developed to become clinically apparent have evolved to evade the immune system (Zitvogel L, et al. Nat Rev Immunol. 2008 8(1):59-73). The notion of increasing the immune system efficacy by therapeutic intervention in order to systemically eradicate cancer cells has long been a vision of oncologists and cancer researchers. A particularly exciting development, hailed by the editors of Science as the scientific breakthrough of 2013 (Couzin-Frankel J. Science. 2013 342 (6165):1432-3), is that novel immunotherapeutic strategies show remarkable responses in some patients, especially if combined with common cytotoxic agents. Radiotherapy and chemotherapeutic agents have been shown to substantially enhance tumor-specific immune responses in well-established tumors (Zitvogel L, et al. Nat Rev Immunol. 2008 8(1):59-73; Reits E A, et al. J Exp Med. 2006 203(5):1259-71; Lugade A A, et al. J Immunol. 2005 174(12):7516-23). The synergy between radiation and immunotherapy stems from radiation-induced (i) immunogenic cell death that locally exposes a wealth of tumor antigens, and (ii) release of stress proteins and danger associated molecular patterns (HSPs, DAMPs), which are endogenous immune adjuvants that can stimulate dendritic cell activation (Vatner R E, et al. Front Oncol. 2014 4:325) (FIG. 13C). Most fascinating is the observation that the stimulation of the immune system by localized radiotherapy may modulate systemic regression of metastatic nodules, which is known as the radiation-induced abscopal effect (Demaria S, et al. Int J Radiat Oncol Biol Phys. 2004 58(3):862-70). Such abscopal responses triggered by localized radiotherapy have been reported among others for lymphomas (Antoniades J, et al. Int J Radiat Oncol Biol Phys. 1977 2(1-2):141-7), renal cell carcinomas (Wersall P J, et al. Acta Oncol. 2006 45(4):493-7), papillary adenocarcinomas (Ehlers G, et al. Br J Radiol. 1973 46(543):220-2), but given the large number of patients with metastatic disease these reports remain considered anecdotal (Kaminski J M, et al. Cancer Treat Rev. 2005 31(3):159-72). Abscopal responses can be triggered more reliably through combining irradiation with immunotherapy (Vatner R E, et al. Front Oncol. 2014 4:325). A strong systemic response against squamous cell carcinoma in mice was observed when dendritic cells where administered intratumorally after local irradiation (Akutsu Y, et al. Int J Oncol. 2007 31(3):509-15).

The possibility of rationally inducing abscopal affects using radiotherapy and immunotherapy has the flavor of the long-sought "magic bullet." But generation of the synergy required to provide local control and to induce the abscopal effect is difficult to predict due to myriad factors including tumor and immune system heterogeneity as well as space and time dependent treatment effects. A wide range of mathematical models has been developed to describe tumor immune interactions at different phases of tumor progression (Kuznetsov V A, et al. Bull Math Biol. 1994 56(2):295-321; Wilkie K P. Adv Exp Med Biol. 2013 734:201-34; d'Onofrio A, et al. Phys Rev E Stat Nonlin Soft Matter Phys. 2011 84(3 Pt 1):031910), or to look at different pathways that are or could be exploited for immunotherapy (Arciero J C, et al. Discret Contin Dyn S. 2004 4(1):39-58; Kirchner D, et al. J Math Biol. 1998 37(3):235-52; Kronik N, et al. PloS one. 2010 5(12):e15482; Kronik N, et al. Cancer Immunol Immunother. 2008 57(3):425-39; Cappuccio A, et al. Cancer Res. 2006 66(14):7293-300), but all focused on a single tumor site. Thus, no prominent inroads have been made to decipher immune-modulated systemic metastatic response triggered by localized radiotherapy.

SUMMARY

Methods for personalized treatment of tumor lesions in subject with metastatic cancer or multiple primary tumors are disclosed. For example, for a subject having a plurality of tumor lesions in two or more organs, the method can be used to select a tumor lesion and/or tumor bearing organ that has the highest chance of producing a systemic abscopal effect after treatment with a localized therapy that induces immunogenic cell death, which triggers an immune response.

In some embodiments, the method involves determining the location and volume for each of the plurality of tumor lesions in the subject. For example, this can involve three-dimensional radiological images of the subject registering geographic locations of each of the plurality of tumor lesions. Non-limiting examples of radiological images that can be used to determine location and/or volume of a tumor lesion include positron emission tomography (PET) scans, x-ray computerized tomography (CT), magnetic resonance imaging (MRI), nuclear magnetic resonance imaging (NMRI), magnetic resonance tomography (MRT), or a combination thereof.

In some embodiments, the method further involves modeling the blood flow dynamics and T cell infiltration probabilities in a single cardiac cycle for each tumor lesion to predict systemic distribution of T cells activated at each tumor lesion. For example, this step can involve comparing the volume of each tumor lesion to the volume of its tumor bearing organ; determining a physiologic blood flow fraction for each tumor bearing organ; calculating for each tumor lesion an infiltration probability that predicts whether a T cell in circulation will infiltrate the tumor lesion in a single circulatory cycle based on the percent of organ taken, the physiologic blood flow fraction of the tumor lesion or the tumor bearing organ, and the extravasation probability for T cells activated in the organ of the tumor lesion, not activated in the organ of the tumor lesion, or a combination thereof; calculating for each tumor lesion a homing probability that predicts the relative number of activated T cells that will home to the tumor lesion based on the infiltration probabilities for each tumor lesion; and calculating for each tumor lesion a homing distribution entropy value that predicts the relative distribution of T cells activated in the tumor lesion based on the total number of tumor lesions and the calculated homing probability for each tumor lesion.

In some embodiments, the method further involves calculating an immunogenicity index value for each tumor lesion based on the predicted homing distribution and volume of each tumor lesion relative to the largest tumor lesion. This immunogenicity index value can predict for which tumor lesion there is a largest likelihood that a local therapy that induces immunogenic cell death in a subject of the tumor lesion will induce a systemic abscopal effect. For example, a large tumor that has non-uniform homing distribution, and a small tumor that has close to uniform homing distribution to each organ compartment would both have lower immunogenicity indexes compared to a large tumor that has close to uniform homing distribution to each tumor bearing organ compartment.

For example, the method can further involve irradiating the tumor lesion(s) in the subject having the highest immunogenicity index. For example, the tumor lesion(s) can be treated with fractionated radiation therapy, hypofractionated radiation therapy, hyperfractionated radiation lesion therapy, single-dose irradiation, stereotactic radiosurgery, or stereotactic body radiation therapy.

The method can also involve the use of an ablative therapy of the tumor lesion(s) having the highest immunogenicity index. Ablative cancer treatments use either heat or cold to destroy, or ablate, cancer tumors without the need for more invasive surgery. Non-limiting examples of ablative therapy include thermal ablation (radiofrequency ablation (RFA), microwave ablation, and non-invasive high intensity focused ultrasound (HIFU) ablation.

The method can also involve the use of local chemotherapeutics through intratumoral administration of chemotherapy, chemotherapy delivered through nanoparticles, or hypoxia-activated prodrugs (HAP). Non-limiting examples of HAP are drug candidates AQ4N (Novacea), PR-104 (Proacta) and TH-302 (Threshold Pharmaceuticals).

The method can also involve treating the subject with local or systemic immunotherapy, chemotherapy, or combination thereof. For example, the method can further involve intratumoral injection of dendritic cells into the tumor lesion(s) having the highest immunogenicity index.

The disclosed methods can be used in any subject with two or more tumor lesions in different organs to identify the best organ to treat and potentially induce an abscopal effect that treats the remaining tumor lesions. In some cases, at least one of the tumor lesions is a metastatic tumor lesion. However, the method can also be used when one or more of the tumor lesions are primary tumors.

In some cases, at least one of the tumor lesions must be treated by a local therapy that induces immunogenic cell death, such as radiotherapy, for medical reasons independent of the desire to promote an abscopal effect. In these cases, the method accounts for this and identifies tumor lesion(s) in the subject having the highest immunogenicity index in view of the preselected tumor lesion. In some cases, this involves identifying tumor lesions having complementarity in homing distribution values with that of the preselected tumor lesion. For example, a tumor that is predicted to home only to the liver may have the highest immunogenicity index when treated in combination with a preselected tumor lesion that homes to every organ compartment other than the liver.

In some cases, multiple tumor lesions may be treated by local therapy that induces immunogenic cell death, such as radiotherapy. In these cases, the method accounts for this and identifies tumor lesion(s) in the subject having the highest immunogenicity index in combination. In some cases, this involves identifying tumor lesions having complementarity in homing distribution values with that of the preselected tumor lesion In some cases, local treatment induced systemic immune response may lead to eradication of circulating tumor cells or un-detectable micro-metastases in different organs.

The disclosed method can also take into account the maximum therapy dosage that each tumor lesion and tumor bearing organ can receive, e.g., due to potential complications in surrounding tissue. This "doseability" can therefore be used in some embodiments to affect the immunogenicity score of the lesion, or possibly disqualify the tumor lesion altogether. In addition, coupling "doseability" with the immunogenicity index might show that in some cases it is better to irradiate two lesions with low "doseability" than one highly "dosable" alone.

Also disclosed is a system for providing a personalized treatment plan for a subject with a plurality of tumor lesions in two or more tumor bearing organs. The system generally comprises a memory operably coupled to the processor, wherein the memory has computer-executable instructions stored thereon that, when executed by the processor, cause the processor to: determine a respective volume of each of the tumor lesions using at least one possibly manually pre-processed radiological image of the subject; obtain a respective physiologic blood flow fraction associated with each of the tumor bearing organs or directly tumor lesions; obtain a respective T cell extravasation probability associated with each of the tumor lesions; calculate a respective homing distribution for each of the tumor lesions based on the respective volume of each of the tumor lesions, the respective physiologic blood flow fraction associated with each of the tumor lesions, and the respective T cell extravasation probability associated with each of the tumor lesions; calculate a respective immunogenicity index value for each of the tumor lesions based on the respective volumes of each of the tumor lesions and the respective homing distributions for each of the tumor lesions; and provide a recommendation for treating one or more of the tumor bearing organs with a therapy that induces immunogenic cell death based on the respective immunogenicity index values for each of the tumor lesions. In some cases, the memory has further computer-executable instructions stored thereon that, when executed by the processor, cause the processor to receive at least one radiological image or the complete radiological data set of the subject.

Non-limiting examples of radiological images that can be used include positron emission tomography (PET) scans, x-ray computer tomography, or a combination thereof.

In some embodiments, calculating the respective homing distribution for each of the tumor lesions comprises calculating a respective infiltration probability for each of the tumor lesions that predicts whether a T cell in circulation will infiltrate each of the tumor lesions in a single circulatory cycle, and wherein the respective infiltration probability for each of the tumor lesions is based on the respective volume of each of the tumor lesions, the respective physiologic blood flow fraction associated with each of the tumor lesions, and the respective T cell extravasation probability associated with each of the tumor lesions.

In some embodiments, calculating the respective homing distribution for each of the tumor lesions comprises calculating a respective homing probability for each of the tumor lesions that predicts the fraction of activated T cells that will home to each of the tumor lesions, and wherein the respective homing probability for each of the tumor lesions is based on the respective infiltration probability for each of the tumor lesions.

In some embodiments, calculating the respective homing distribution for each of the tumor lesions comprises calculating a respective homing distribution entropy value for each of the tumor lesions that predicts the relative distribution of T cells activated in each of the tumor lesions, and wherein the respective homing distribution entropy value for each of the tumor lesions is based on a total number of the tumor lesions and the respective homing probability for each of the tumor lesions.

In some embodiments, the respective immunogenicity index value for each of the tumor lesions is based on the respective homing distribution entropy value for each of the tumor lesions and the respective volume of each of the tumor lesions.

In some embodiments, the respective T cell extravasation probability comprises a probability of T cells activated in a tumor bearing organ of each of the tumor lesions, not activated in the tumor bearing organ of each of the tumor lesions, or a combination thereof.

In some embodiments, the memory has further computer-executable instructions stored thereon that, when executed by the processor, cause the processor to calculate a respective volume ratio of: (i) the respective volume of each of the tumor lesions to (ii) a volume of a tumor bearing organ of each of the tumor lesions, wherein the respective volume ratio for each of the tumor lesions is used in the calculation of the respective immunogenicity index value for each of the tumor lesions.

In some embodiments, the memory has further computer-executable instructions stored thereon that, when executed by the processor, cause the processor to calculate a respective blood flow fraction ratio of: (i) the respective physiologic blood flow fraction associated with each of the tumor lesions to (ii) a respective physiologic blood flow fraction associated with a compartment of each of the tumor lesions, wherein the respective blood flow fraction ratio for each of the tumor lesions is used in the calculation of the respective immunogenicity index value for each of the tumor lesions.

In some embodiments, the respective immunogenicity index values for each of the tumor lesions predicts which of the lesions has the highest likelihood that treating each of the tumor lesions with a targeted therapy that induces immunogenic cell death will induce an abscopal effect. For example, the recommendation can be to treat a tumor bearing organ with the highest likelihood of inducing the abscopal effect. As another example, the recommendation can be to treat a plurality of tumor bearing organs with the combined highest likelihood of inducing the abscopal effect.

In some embodiments, the memory has further computer-executable instructions stored thereon that, when executed by the processor, cause the processor to consider a first preselected tumor bearing organ as a necessary target for treatment and provide a recommendation for irradiating a second tumor bearing organ having tumor lesions with the highest immunogenicity index in view of a preselected tumor bearing organ.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 9 shows equations for a multiscale model of lymph nodes and metastasis.

FIG. 11 is a proposed mathematical model of the interplay between tolerogenic T cells, immunogenic T cells, effector T cells, and Tregs.

FIG. 13A depicts activated cytotoxic T cell (CTL) entering the blood system via great veins, flowing through the pulmonary circulation, and then going into systemic circulation. Venous blood from gastrointestinal tract and spleen goes to the liver through hepatic portal vein. FIG. 13B illustrates that in each compartment CTL can flow through without reaching the tumor site or enter one of metastatic sites (circles) and extravasate into the tissue. FIG. 13C illustrates how radiotherapy (RT) triggers immunogenic cells that activate dendritic cells (DCs) that then travel to lymph nodes. DCs transform naïve T cells into CTLs, which, in case of non-metastatic disease, travel back through the blood system to the tumor site to exert their cytotoxic effects.

DETAILED DESCRIPTION

Disclosed herein is a tumor-immune system interactions modeling framework that incorporates a mathematical model of activated T cell trafficking between metastatic sites. As disclosed herein, an abscopal response can be achieved when T cells that are locally activated by radiotherapy (or any other treatment inducing immunogenic cell death) are systemically distributed among the metastatic sites in numbers sufficient to tip immune surveillance back in favor of tumor eradication at each metastatic site. Trafficking and distribution of activated T cells are shown to strongly depend on the geographic distribution of metastatic sites, physiologic blood flow fractions to tumor bearing organs, tumor burden in each metastatic tissue, and the strength of immune cell homing cues. Different metastatic sites may have varying potential to trigger a systemic response. On the basis of the T cell homing distribution optimum treatment targets were determined in a virtual clinical trial. A model of tumor-immune interactions was incorporated into the framework to simulate local tumor growth of each metastasis. This provides insights into the tumor growth and treatment response dynamics.

Figure 18:
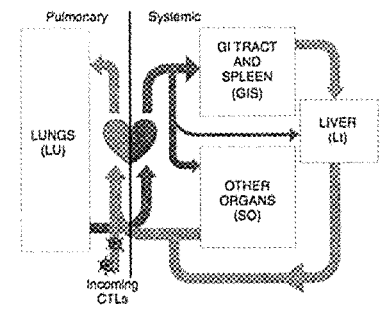
FIG. 18 is a flowchart depicting an example process for calculating an immunogenicity score for each tumor site that predicts the optimal site(s) for radiation therapy to promote an abscopal effect.

FIG. 18 is a flowchart depicting an example process for calculating an immunogenicity score for each tumor site that predicts the optimal site(s) for radiation therapy to promote an abscopal effect. The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

This disclosed method can be used to predict which of the lesion has the highest likelihood that a targeted therapy that induces immunogenic cell death in a subject of the tumor lesion will induce an abscopal effect. Targeted therapies used to induce cytoimmunogenic cell death in tumors include radiotherapy and ablative therapies. Ablative cancer treatments use either heat or cold to destroy, or ablate, cancer tumors without the need for more invasive surgery. Non-limiting examples of ablative therapy include thermal ablation (radiofrequency ablation (RFA), microwave ablation, and non-invasive high intensity focused ultrasound (HIFU) ablation.

Radiation therapy, radiotherapy, or radiation oncology is therapy using ionizing radiation, generally as part of cancer treatment to control or kill malignant cells. Radiation may be prescribed by a radiation oncologist for curative, adjuvant, neoadjuvant, therapeutic, or palliative treatment. It is also common to combine radiation therapy with surgery, chemotherapy, hormone therapy, immunotherapy or some mixture of the four. Most common cancer types can be treated with radiation therapy in some way. The precise treatment intent (curative, adjuvant, neoadjuvant, therapeutic, or palliative) will depend on the tumor type, location, and stage, as well as the general health of the patient. Total body irradiation (TBI) is a radiation therapy technique used to prepare the body to receive a bone marrow transplant. However, the disclosed methods generally involve the use of targeted, localized radiation therapy to promote an abscopal effect. Brachytherapy, in which a radiation source is placed inside or next to the area requiring treatment, is another form of radiation therapy that minimizes exposure to healthy tissue during procedures to treat cancers of the breast, prostate and other organs.

The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy. Preventive (adjuvant) doses are typically around 45-60 Gy in 1.8-2 Gy fractions (for breast, head, and neck cancers.) Many other factors are considered by radiation oncologists when selecting a dose, including whether the patient is receiving chemotherapy, patient comorbidities, whether radiation therapy is being administered before or after surgery, and the degree of success of surgery.

Delivery parameters of a prescribed dose are determined during treatment planning (part of dosimetry). Treatment planning is generally performed on dedicated computers using specialized treatment planning software. Depending on the radiation delivery method, several angles or sources may be used to sum to the total necessary dose. The planner will try to design a plan that delivers a uniform prescription dose to the tumor and minimizes dose to surrounding healthy tissues.

The total dose is fractionated (spread out over time) for several important reasons. Fractionation allows normal cells time to recover, while tumor cells are generally less efficient in repair between fractions. Fractionation also allows tumor cells that were in a relatively radioresistant phase of the cell cycle during one treatment to cycle into a sensitive phase of the cycle before the next fraction is given. Similarly, tumor cells that were chronically or acutely hypoxic (and therefore more radioresistant) may reoxygenate between fractions, improving the tumor cell kill.

In North America, Australia, and Europe, the standard fractionation schedule for adults is 1.8 to 2 Gy per day, five days a week. In some cancer types, prolongation of the fraction schedule over too long can allow for the tumor to begin repopulating, and for these tumor types, including head-and-neck and cervical squamous cell cancers, radiation treatment is preferably completed within a certain amount of time. For children, a typical fraction size may be 1.5 to 1.8 Gy per day, as smaller fraction sizes are associated with reduced incidence and severity of late-onset side effects in normal tissues.

In some cases, two fractions per day are used. This schedule, known as hyperfractionation, is used on tumors that regenerate more quickly when they are smaller. In particular, tumors in the head-and-neck demonstrate this behavior. One fractionation schedule that is increasingly being used and continues to be studied is hypofractionation. This is a radiation treatment in which the total dose of radiation is divided into large doses. Typical doses vary significantly by cancer type, from 2.2 Gy/fraction to 20 Gy/fraction. The logic behind hypofractionation is to lessen the possibility of the cancer returning by not giving the cells enough time to reproduce and also to exploit the unique biological radiation sensitivity of some tumors. One commonly treated site where there is very good evidence for such treatment is in breast cancer.

One of the best-known alternative fractionation schedules is Continuous Hyperfractionated Accelerated Radiation therapy (CHART). CHART, used to treat lung cancer, consists of three smaller fractions per day. Although reasonably successful, CHART can be a strain on radiation therapy departments.

Another increasingly well-known alternative fractionation schedule, used to treat breast cancer, is called Accelerated Partial Breast Irradiation (APBI). APBI can be performed with either brachytherapy or with external beam radiation. APBI normally involves two high-dose fractions per day for five days, compared to whole breast irradiation, in which a single, smaller fraction is given five times a week over a six-to-seven-week period. An example of APBI where the entire dose is delivered in a single fraction is TARGIT.

The methods provided herein can be performed with any suitable radiotherapy, including, but not limited to, external beam radiotherapy, also known as teletherapy; sealed source radiotherapy, also known as brachytherapy; unsealed source radiotherapy; radioisotope therapy; and radioimmunotherapy.

In some embodiments, the radiotherapy is external radiation therapy. Examples of external radiation therapy include, but are not limited to, conventional external beam radiotherapy; three-dimensional conformal radiation therapy (3D-CRT), which delivers shaped beams to closely fit the shape of a. tumor from different directions; intensity modulated radiation therapy (IMRT), e.g., helical tomotherapy, which shapes the radiation beams to closely fit the shape of a tumor and also alters the radiation dose according to the shape of the tumor; conformal proton beam radiation therapy; image-guided radiotherapy (IGRT), which combines scanning and radiation technologies to provide real time images of a tumor to guide the radiation treatment; intraoperative radiation therapy (IORT), which delivers radiation directly to a tumor during surgery; stereotactic radiosurgery, which delivers a large, precise radiation dose to a small tumor area in a single session; hyperfractionated radiotherapy, e.g., continuous hyperfractionated accelerated radiotherapy (CHART), in which more than one treatment (fraction) of radiotherapy are given to a subject per day; and hypofractionated radiotherapy, in which larger doses of radiotherapy per fraction is given but fewer fractions.

In another embodiment, the radiotherapy is internal radiation therapy. Example of internal radiation therapy include, but are not limited to, interstitial, intracavitary, intraluminal, intravenously radiation therapy, and implant radiation therapy, such as implantation of radioactive beads, particles, or seeds. In some embodiments, the radiotherapy is sealed source radiotherapy. In another embodiment, the radiotherapy is unsealed source radiotherapy.

In yet another embodiment, the radiotherapy is radioisotope therapy or radioimmunotherapy, where the radiotherapy is performed by administering a radioisotope parenterally to a subject, e.g., by injecting to a subject a tumor-specific antibody-radioisotope conjugate. Suitable radioisotopes for radioisotope therapy or radioimmnunotherapy include, but are not limited to, $^{72}$As, $^{198}$Au, $^{206}$Bi, $^{77}$Br, $^{11}$C, $^{14}$C, $^{47}$Ca, $^{129}$Ce, $^{137}$Ce, $^{55}$Co, $^{56}$Co, $^{57}$Co, $^{58}$Co, $^{60}$Co, $^{51}$Cr, $^{61}$Cu, $^{169}$Er, $^{18}$F, $^{52}$Fe, $^{55}$Fe, $^{59}$Fe, $^{67}$Ga, $^{123}$I, $^{125}$I, $^{131}$I, $^{111}$In, $^{192}$Ir, $^{81}$Kr, $^{177}$Lu, $^{52}$Mg, $^{13}$N, $^{22}$Na, $^{24}$Na, 57Ni, $^{15}$O, $^{32}$P, $^{203}$Pb, $^{103}$Pd, $^{81}$Rb, $^{72}$Se, $^{73}$Se, $^{75}$Se, $^{153}$Sm, $^{89}$Sr, $^{90}$Sr, T, $^{99}$Tc, $^{201}$Tl, $^{167}$Tm, $^{90}$Y, $^{62}$Zn, and $^{133}$Xe. Examples of reagents for radioisotope therapy and radioimmunotherapy include, but not limited to, metaiodobenzylguanidine, oral iodine-131, hormone-bound lutetium-177 and yttrium-90, ibriturnornab tiuxetan, tositumotnab iodine-131, radioactive glass or resins, and radioactive nanoparticles.

The choice of the radiation therapy can be determined by taking into consideration various factors, including, e.g., the type, size, and location of the tumor, the age, weight, and condition of the subject being treated. It is understood that the precise dose of the radiation and duration of treatment may vary with the age, weight, and condition of the subject being treated, and may be determined empirically using known testing protocols or by extrapolation from in vivo or in vitro test or diagnostic data. It is also understood that the total radiation dose required is often divided into two or more fractions, which are administered over an extended period of time. It is further understood that for any particular individual, specific dosage regimens could be adjusted over time according to the individual need and the professional judgment of the person administering or supervising the administration of the radiation.

In some embodiments, the total dose given in the radiotherapy is ranging from about 40 Gy to about 80 Gy. In certain embodiments, the total dose is divided into fractions and each fraction can be the same or different. Each fraction ranges from about 0.5 Gy to about 50 Gy.

In some embodiments, the subject of the disclosed methods is further treated with an immunotherapy to enhance the abscopal effect. For example, dendritic cells (DCs) represent unique antigen-presenting cells capable of activating T cells to both new and recall antigens. In fact, these cells are the most potent antigen-presenting cells. The goal of DC based cancer immunotherapy is to use the cells to prime specific antitumor immunity through the generation of effector cells that attack and lyse tumors. Therefore, in some embodiments, the disclosed methods further involve administering DCs to the subject. In some embodiments, the DCs are administered directly to the tumor lesion site(s) being irradiated. In some embodiments, the DCs are administered systemically or to tumor site(s) in addition to or distinct from the sites being irradiated.

Additional immunotherapeutic approaches include 1) use of exogenous cytokines to non-specifically stimulate the immune system's effector cells to mount an anti-tumor response, 2) introduction of immuno-stimulatory antigens to precipitate a targeted immune response (i.e. active immunization or tumor vaccination), 3) exogenous expansion and reinfusion of tumor-specific immune cells (adoptive immunotherapy), 4) immune system checkpoint modulation, and 5) use of cancer-killing and immune system-stimulating modified viruses (oncolytic immunotherapy). Vaccination with telomerase vaccine (GV1001) can be combined with an immune adjuvant, e.g., granulocyte macrophage colony-stimulating factor (GM-CSF), and a cycle of gemcitabine chemotherapy.

Immunostimulatory cytokines include interferon alpha (IFN-α) and interleukin-2 (IL-2). IFN-α directly inhibits tumor cell proliferation, enhances innate & adaptive immunity, facilitates tumor antigen recognition via enhanced MHC I receptor expression, represses oncogenes and induces tumor suppressor gene expression, and inhibits angiogenesis. IL-2 activates B, T, & NK cells, and facilitating cytolytic destruction of tumor cells Anticancer vaccines can facilitate tumor antigen recognition and a subsequent anti-tumor immune response by artificially introducing tumor-associated antigens to the body, or cellular equipment that can help expose those already present. Artificially introduced antigens can take the form of peptide fragments, whole proteins, cell lysates or whole cells. For example, telomerase is highly expressed in essentially all cancer forms, while the expression in normal tissues is restricted. Moreover, telomerase activity is considered indispensable for tumor immortalization and growth. Human telomerase reverse transcriptase (hTERT), the rate-limiting subunit of the telomerase complex, is therefore an attractive target for cancer vaccination. GV1001, a peptide vaccine representing a 16-aa hTERT sequence, binds multiple HLA class II molecules and harbors putative HLA class I epitopes. The peptide may therefore elicit combined CD4/CD8 T-cell responses, considered important to initiate tumor eradication and long-term memory.

Adoptive cell therapy (ACT) involves harvesting autologous lymphocytes from a patient's tumor or peripheral blood, expanding them and possibly modifying them in-vitro to express tumor-associated antigen receptors or secrete specific cytokines, and reintroducing them back into the host. The adoptive transfer of autologous tumor infiltrating lymphocytes (TIL) or in vitro re-directed peripheral blood mononuclear cells has been used to successfully treat patients with advanced solid tumors, including melanoma and colorectal carcinoma, as well as patients with CD19-expressing hematologic malignancies.

Immunomodulatory monoclonal antibody (mAb) therapies include cytotoxic T-Lymphocyte Antigen-4 (CTLA-4) inhibition (e.g., ipilimumab), Programmed Death-1 (PD-1) inhibition (e.g., nivolumab and pembrolizumab), CD40 agonism, OX40 agonism, Lymphocyte Activation Gene-3 (LAG-3) and T cell Immunoglobulin Mucin-3 (TIM-3) inhibition, and Toll-like receptor agonists. CTLA-4 is a T cell receptor that naturally interacts with B7-1 (CD-80) and B7-2 (CD-86) on the surface of antigen presenting cells, thereby down-regulating the T cell response and avoiding potential autoimmune damage. A costimulatory T cell surface protein, CD-28, on the other hand, competes with CTLA-4, albeit with less affinity, for interaction with B7-1 and B7-2, activating the T cell. Blocking CTLA-4 thereby allows CD-28 to interact with B7-1 and B7-2, enhancing the body's cellular immune response and ability to eradicate tumor cells. For poorly immunogenic tumors, CTLA-4 blockade may be effective if used in combination with vaccination with irradiated tumor cells modified to produce GM-CSF.

PD-1 receptor is expressed on B, T, and NK cells, and interacts with Programmed Death Ligands-1 and -2 (PDL-1 and -2), often subversively expressed on melanoma cells, to induce T cell exhaustion and down-regulate the immune response. By blocking PD-1, these medications facilitate a more vigorous anti-tumor cellular immune response. CD40 is a costimulatory receptor of the tumor necrosis factor (TNF) family normally expressed on a variety of cells including dendritic cells and macrophages. Interaction with its ligand plays a key role in priming and proliferation of antigen-specific CD4 T cells. When expressed on tumor cells, its stimulation results in apoptosis. Thus, CD40-stimulating mAbs (e.g., CD-870873) have direct anti-tumor activity and induce tumor antigen-specific T cell responses. LAG-3 is a transmembrane protein expressed on T regulatory (T reg) cells that binds MHC II, often expressed on melanoma cells, thereby enhancing T reg activity, negatively regulating the cellular immune response, and protecting melanoma cells from apoptosis. Blocking LAG-3 could thus help the body fight tumor cells on two fronts. Another class of immunomodulators act upon TLRs, a group of cell-surface receptors found on sentinel immune cells like dendritic cells and macrophages that naturally activate an innate immune response upon contact with characteristic pathogen-related antigens. Topical treatment of melanoma with Imiquimod (IMQ), a TLR-7 agonist, has been shown to facilitate 1) tumor infiltration with immune effector cells such as activated, cytotoxic plasmacytoid DCs, 2) a type I IFN response, 3) anti-angiogenic defenses, and in some cases result in complete tumor regression.

The blockade of TGF-β by anti-TGF-β antibody can synergistically enhance tumor vaccine efficacy, which is mediated by CD8+ T cells. For example, fresolimumab is an antibody capable of neutralizing all human isoforms of transforming growth factor beta (TGFβ) and has demonstrated anticancer activity.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

Numerous anti-cancer drugs are available for combination with the present method and compositions. The following is a non-exhaustive lists of anti-cancer (anti-neoplastic) drugs that can be used in conjunction with irradiation: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The term "abscopal effect" refers to a phenomenon in the treatment of metastatic cancer where localized irradiation of a tumor causes not only a shrinking of the irradiated tumor but also a shrinking of tumors outside the irradiated area.

The term "subject" refers to any individual who is the target of administration or treatment. The subject can be a vertebrate, for example, a mammal Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "neoplastic cell" or "neoplasm" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor. Neoplasms may be benign, premalignant, or malignant.

The term "cancer" or "malignant neoplasm" refers to a cell that displays uncontrolled growth, invasion upon adjacent tissues, and often metastasis to other locations of the body.

The term "tumor" refers to an abnormal mass of tissue containing neoplastic cells.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

A number of embodiments of the invention have been described. Nevertheless, it will be understood that various modifications may be made without departing from the spirit and scope of the invention. Accordingly, other embodiments are within the scope of the following claims.

EXAMPLES

Figure 1:
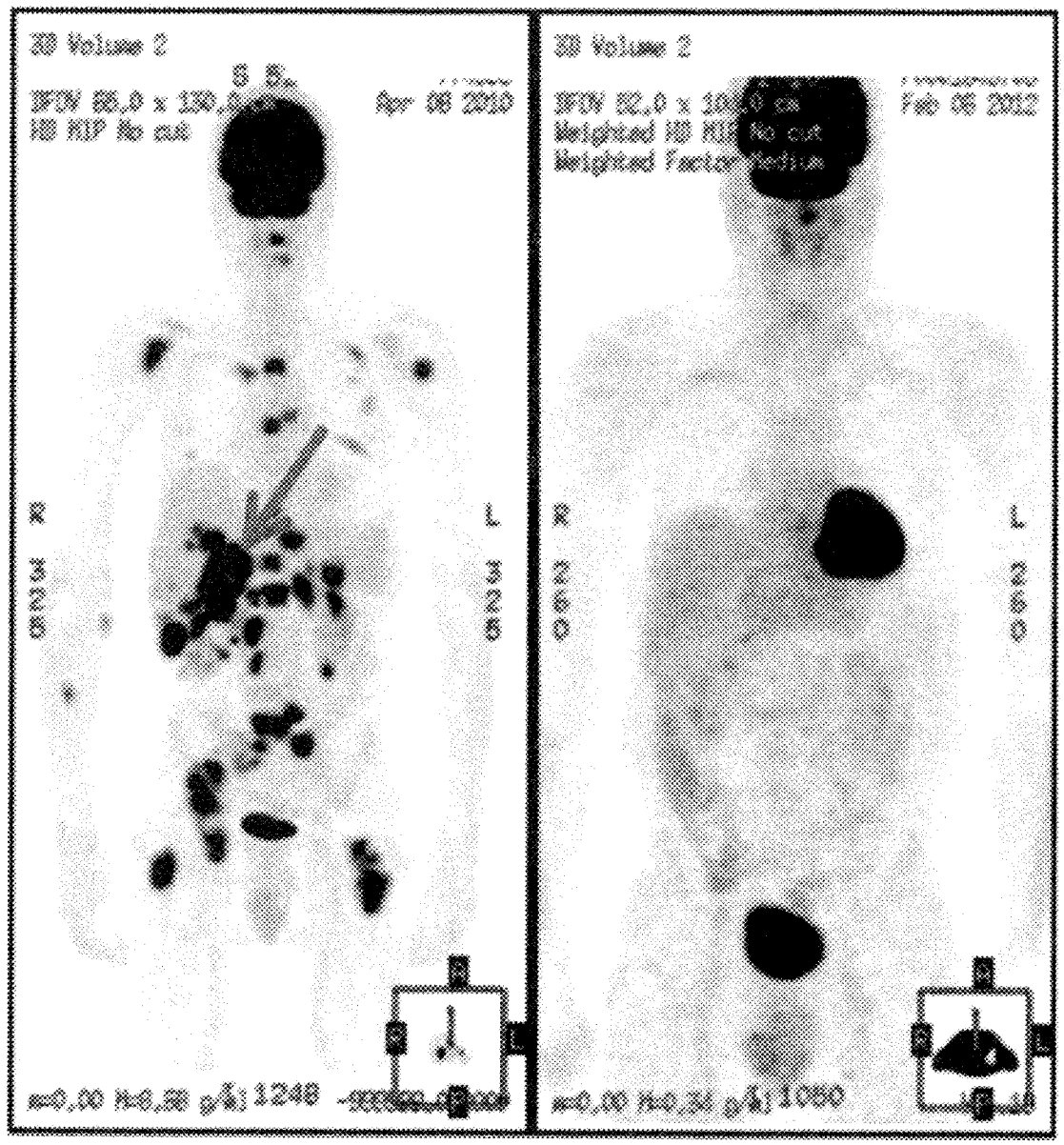
FIG. 1 shows images of pre-and post-treatment PET of a patient with metastatic melanoma. Two liver lesions (arrow) were treated with radiation therapy (20Gy/fraction) followed by systemic high-dose IL-2.
Figure 2:
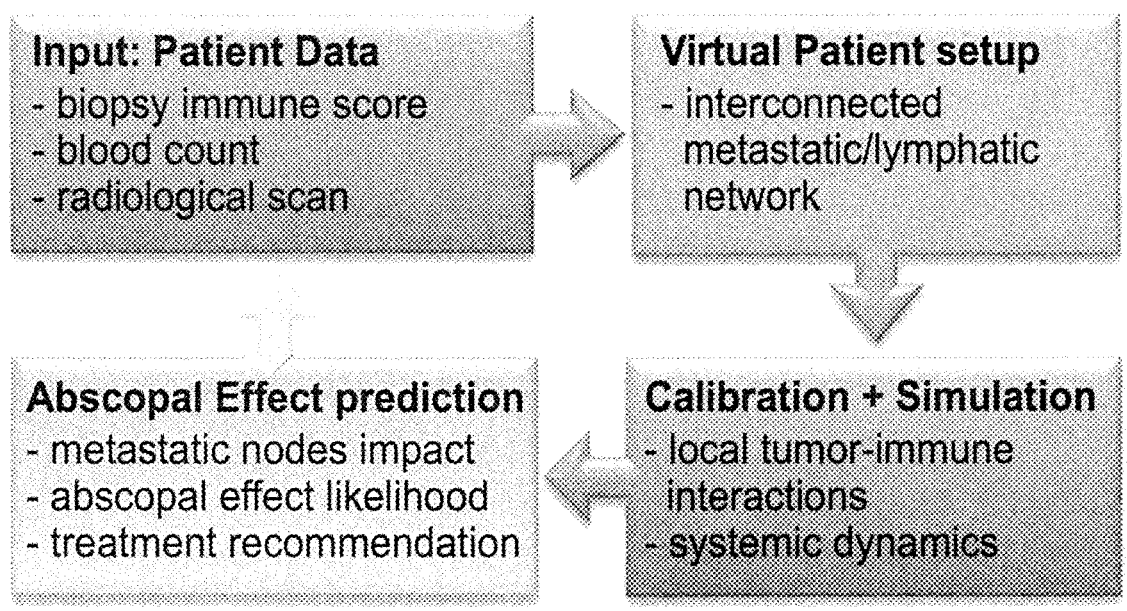
FIG. 2 is a diagram of a research design to make treatment recommendations and predict the likelihood of abscopal effects.

As disclosed herein, the key to inducing a patient-specific abscopal effect is determining the interconnectivity of metastatic nodules and host circulatory system through integration of radiological scans and laboratory tests with quantitative modeling. Disclosed is an integrative framework that translates personalized data into a 'virtual patient'. Patient-specific treatment simulations can then be performed to predict personalized outcomes (FIG. 2). A preliminary framework design successfully reproduced the clinical outcome of one metastatic melanoma patient. This approach can be further developed, calibrated, and validated with samples of patients with different clinical responses.

Example 1

Quantifying T Cell Trafficking to Identify Patient-Specific Irradiation Targets That Trigger Abscopal Responses Equations Metastatic cancer is considered with N distinct tumors located in different organs. The cancer population at each metastatic site, $C_i(t)$, is assumed to follow logistic growth with site dependent carrying capacity, $K_i$, and growth rate, $r_i$, modulated by the predation of immunocompetent effector cells, $E_i(t)$. The equation governing each metastatic site growth is $$\frac{dC_i}{dt} = r_i C_i \left(1 - \frac{C_i}{K_i}\right) - ap E_i C_i. \quad \text{A)}$$

A detailed description of all variables and rate constants with specific values can be found in Table 1.

TABLE 1

Parameter values for the differential part of the model, equations (A) and (B).

| Parameter | Value | Unit | Description |
|---|---|---|---|
| r | 0.188 | 1/day | Maximal tumor growth rate |
| K | 531.91 × 10⁶ | cells | Carrying capacity |
| a | 0.139 × 10⁻⁶ | 1/day/cells | T cell - cancer cell interactions constant |
| p | 0.998 | non-dimensional | Probability that during the interaction between T cell and cancer cell the later will be killed |
| λ | 0.591 | 1/day | Effector cells decay rate |
| E* | 0.3 × 10⁶ | cells | Physiological level of effector cells |
| f | 0.525 if t > 28 days and 0 otherwise | 1/day/cells | Magnitude of immune system stimulation by the presence of cancer cells |
| g | 0.161 × 10⁶ | cells | Immune stimulation damping coefficient |

NOTE:
C(t) measures cell number, but in the T cell trafficking part of the model its value is used in terms of tumor volume in milliliters according to the formula $V(C(t)) = C(t) \times (4/3 \pi r^3) \times 10^{-12}$ mL, where r is the diameter of the cell assumed to be equal 10 micrometers.

Figures 13A, 13B, 13C:
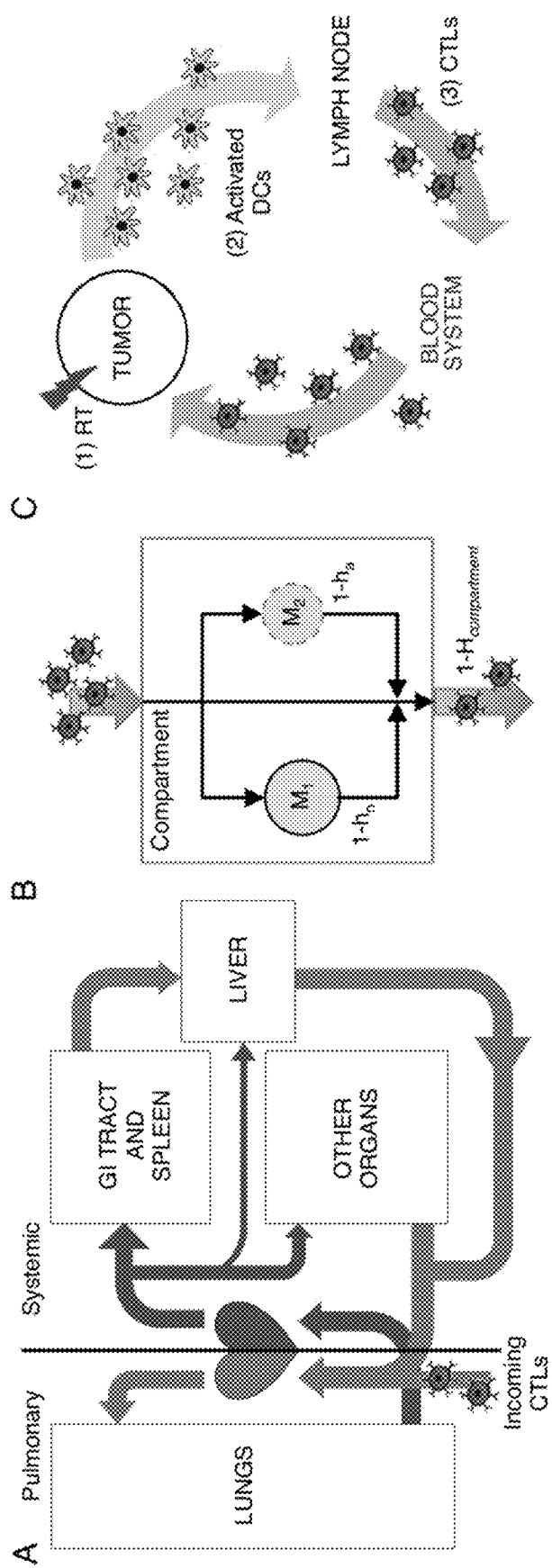
FIGS. 13A to 13C illustrate the process of activated T cell trafficking.

Effector cells are recruited endogenously as well as in relation to tumor burden, and undergo spontaneous decay or exhaust from interactions with cancer cells. Cells that are recruited in response to the tumor presence are mainly the cytotoxic T lymphocytes, key component of the adaptive part of the immune system. The equation governing the population of tumor infiltrating effector cells at each of the metastatic sites is $$\frac{dE_i}{dt} = \lambda(T^* - E_i) - a(1-p)E_i C_i + \sum_{j=1}^{N} \omega_{ij}(\vec{C}) \frac{fC_j}{g + C_j} E_j, \quad \text{B)}$$

where functions $\omega_{ij}(C_1, \ldots, C_N)$ describe the probabilities that cytotoxic T cells activated at site j will infiltrate the ith tumor site. After being activated in the tumor draining lymph node, T cells travel through the lymphatic system, enter the blood circulation, and travel in cycles with blood through the system of arteries, capillaries and veins. To quantify T cell movement in the blood four major coarse-grain flow compartments were distinguished: pulmonary circulation (LU); gastro-intestinal tract and spleen (GIS); liver (LI); and all other organs in the systemic circulation (SO). The distinct consideration of LU, GIS, and LI is important as venous blood from GIS flows through LI through the hepatic portal vein before getting re-oxygenated in LU (FIG. 13A). T cell trafficking between compartments is based on the anatomy with rates being equal to physiological values of blood flow fractions (BFFs, % of cardiac output reaching to the compartment). As described herein, BFFs for compartments (e.g., LU, LI, GIS, SO compartments), as well as BFFs for individual organs can be obtained/calculated according to techniques known in the art. This disclosure contemplates that BFFs can be stored in the memory of a computing device (e.g., the computing device of FIG. 19). For example, the BFFs can optionally be stored in a table and references as needed. $H_{compartment}$ is denoted as the probability that the T cell will be absorbed by one of tumor-harboring tissues after entering a given compartment (FIG. 13B), i.e. $H_{compartment} = \Sigma P_i$, where $P_i$ is the probability that the T cell will infiltrate ith tumor site in a given compartment. The probability of T cell absorption by a given compartment was calculate using a Markov Chain approach $$P_{absorption} = \frac{1}{\Delta} \begin{cases} H_{LU} & \text{at } LU \text{ compartment,} \\ H_{LI}(1 - H_{LU})(BFF_{LI} + BFF_{GIS}(1 - H_{GIS})) & \text{at } LI \text{ compartment,} \\ H_{GIS} BFF_{GIS}(1 - H_{LU}) & \text{at } GIS \text{ compartment,} \\ H_{SO} BFF_{SO}(1 - H_{LU}) & \text{at } SO \text{ compartment,} \end{cases}$$

where $\Delta$ is a normalizing constant, i.e. such that the sum of absorption probabilities over all four compartments is equal to one. T cell decay in the blood system was not consider and, thus each T cell will be eventually absorbed in one of the compartments, with the average number of systemic circulation cycles before absorption equal to $$N_{cycles} = \frac{1}{\Delta} = \frac{1}{H_{LU} + (1 - H_{LU})[H_{LI}(BFF_{LI} + BFF_{GIS}(1 - H_{GIS})) + H_{GIS} BFF_{GIS} + H_{SO} B}} \quad \text{C)}$$

It was assumed that the probability of T cell infiltrating ith tumor site, $P_i$, is equal to the probability that the T cell will flow through the tumor site multiplied by the probability of extravasation from blood to the tissue, h. The former was approximated using the relative blood flow through a specific tumor bearing organ (e.g., a ratio of $BFF_{organ}$ to $BFF_{compartment}$) multiplied by the fraction of organ (e.g., a ratio of $V^i$ to $V^i_{organ}$) taken and, thus, the equation describing $P_i$ is $$P_i = h \times \frac{BFF^i_{organ}}{BFF^i_{compartment}} \times \frac{V^i}{V^i_{organ}}.$$

The volume of a tumor ($V^i$) can be determined from radiological image(s) of the subject, for example, using image processing techniques known in the art including, but not limited to, volume rendering. Additionally, the volume of the tumor-bearing organ ($V^i_{organ}$) can similarly be determined from radiological image(s) of the subject. It should be understood that determination of the volume of the tumor-bearing organ from radiological image(s) of the subject will account for subject-specific differences in volume. Alternatively or additionally, the volume of the tumor-bearing organ ($V^i_{organ}$) can be the average volume of a tumor-bearing organ as known in the art as described herein. This disclosure contemplates that organ volumes can be stored in the memory of a computing device (e.g., the computing device of FIG. 19). For example, the average organ volumes can optionally be stored in a table and references as needed. For example, in PET images gross tumor volumes can by automatically delineated using a segmentation algorithm based on the measured signal-to noise ratio (Daisne J F, et al. Radiother Oncol. 2003 (69): 247-150).

Experimental studies clearly show that during the activation process in the lymph node T cells are programmed to express homing molecules specific to the site of the immunization (Mikhak Z, et al. J Exp Med. 2013 210(9):1855-69; Calzascia T, et al. Immunity. 2005 22(2):175-84). Thus it was assumed that $h=h_a$ if the T cell was activated in the given organ, and $h=h_n$ otherwise ($1 \geq h_a > h_n$). Probabilistic model defined above allows to calculate functions $\omega_{ij}(C_1, \ldots, C_N)$ in the effector cells dynamics equation (B) for different geographic distribution of metastatic disease.

Materials and Methods

The different components of the mathematical framework were calculated or solved numerically in MATLAB (www.mathworks.com).

Model Parameters Estimation

The gastro-intestinal tract consist mainly of stomach, esophagus, intestine and pancreas, with physiological blood flow fractions (BFFs) of 1%, 16% and 1%, respectively (Valentin J. Annals of the ICRP. 2002 32(3-4):1-277). BFF to the spleen is estimated to be 3% (Valentin J. Annals of the ICRP. 2002 32(3-4):1-277), which together yields $BFF_{GIS}=21\%$. It is estimated that the internal mammalian artery with the average blood flow of 59.9 mL/min, provides about 60% of breast blood supply. With an average cardiac output of 300 L/h (Abduljalil K, et al. Clin Pharmacokinet. 2012 51(6):365-96), BFF to the breast ($BFF_{breast}$) was estimated to be 2%. BFF to the kidney ($BFF_{kidney}$) was estimated to be 8.5% (Valentin J. Annals of the ICRP. 2002 32(3-4):1-277).

In a study performed by Mikhak et al. (Mikhak Z, et al. J Exp Med. 2013 210(9):1855-69), T cells isolated from mice transgenic for the TCR recognizing ovalbumin (OVA, antigen) were activated in vitro with dendritic cells (DCs) isolated from different mouse tissues including lung, thoracic lymph nodes and skin. Populations of activated T cells were then injected into naïve mice and challenged with aerosolized OVA. 24 h after the last challenge mice were sacrificed and lung tissue harvested. The number of T cells measured was about 3 times larger compared to other groups when T cells where activated with lung DSc. Thus, the extravasation probability of T cell to the tissue of activation ($h_a$) was estimate to be three times larger than extravasation into non-activation tissue sites ($h_n$; $h_n/h_a=1/3$). Values of other parameters associated with T cell trafficking, i.e. those that are necessary to calculate values of $\omega_{ij}(C_1, \ldots, C_N)$, were taken from literature and are summarized in Table 2.

TABLE 2

Parameter values for the T cell trafficking part of the model.

| Parameter | Value | Description | Reference |
|---|---|---|---|
| $BFF_{LI}$ | 6.5% | Blood flow fraction to liver | Valentin J. Annals of the ICRP. 2002 32(3-4): 1-277 |
| $BFF_{GIS}$ | 21% | Blood flow fraction to gastro-intestinal tract and spleen | estimated |
| $BFF_{SO}$ | 72.5% | Blood flow fraction to SO compartment | by definition = 100% − $BFF_{LI}$ − $BFF_{GIS}$ |
| $BFF_{breast}$ | 2% | Blood flow fraction to the breast | estimated |
| $BFF_{kidney}$ | 8.5% | Blood flow fraction to the kidney | Valentin J. Annals of the ICRP. 2002 32(3-4): 1-277 |
| $V_{liver}$ | 1493 mL | Average liver volume | Henderson J M, et al. Radiology. 1981 141(2): 525-7 |
| $V_{breast}$ | 500 mL | Average breast volume | Abduljalil K, et al. Clin Pharmacokinet. 2012 51(6): 365-96 |
| $V_{lungs}$ | 3679 mL | Average lung volume | Puybasset L, et al. Am J Respir Crit Care Med. 1998 158(5 Pt 1): 1644-55 |
| $V_{kidney}$ | 249 mL | Average kidney volume | Poggio E D, et al. Am J Transplant. 2006 6(3): 616-24 |

Virtual Case Studies and Immunogenicity Quantification

C cohort was create of 40 virtual metastatic patients with arbitrary combinations of breast, liver, kidney and lung metastases of random sizes between 50 and 300 cc. Systemic T cells trafficking was investigate for different sites of T cell activation via local radiotherapy with fixed dose to different individual metastatic sites. The T cells dissemination quality for different sites of activation was evaluated by comparing the values of the entropy of established homing distribution scaled by the maximum attainable entropy $$S_i = \left(\sum_{j=1}^{N} p_{ji} \ln p_{ji}\right) \bigg/ \left(N \ln \frac{1}{N}\right), \quad \text{D)}$$

where i is the site of activation, and $p_{ij}$ is the probability that T cell activated at site i will infiltrate tumor at site j. The immunogenicity index, reminiscent of the probability of triggering an abscopal effect, was define by additionally taking into account the size of the tumor relative to other sites $$I_i = S_i \frac{V_i}{\max(V_1, \ldots, V_N)}. \quad \text{E)}$$

Tumor size plays a crucial role as irradiation of larger tumors leads to more cells undergoing immunogenic cell death, which translates into local immune activation. The maximum immunogenicity index of one (1) can only be achieved theoretically if the largest tumor is treated and the distribution of activated T cells was uniform between the metastatic sites. For expected non-uniform distributions of activated T cells, however, the tumor size alone is insufficient to predict immunogenicity indices.

Simulation of Experimental Metastatic Disease Progression

Breast cancer growth was initiated with $0.5 \times 10^6$ cancer cells and tumor growth simulated. After 200 days the onset of a metastasis was simulated by initiating a population of $0.5 \times 10^6$ cancer cells in the lung, and growth of both tumor sites simulated for another 200 days. For illustration purpose, the growth rate of the lung tumor was assumed to be twice as fast as the breast tumor, what might reflect better oxygen availability in the lung. Extravasation probabilities $h_a$ and $h_n$ were assumed to be equal 0.6 and 0.2, respectively.

Simulation of Primary Tumor Removal

After simulating the primary tumor growth in the breast and further progression of the metastatic site in the lung we simulate complete surgical removal of the primary breast tumor by instantaneously removing both cancer cells and T cells populations present in the breast. Parameters describing dynamics of the lung metastasis remain unchanged.

Results

Variation in Immunogenicity Between Metastatic Sites

A detailed analysis is provided of the first out of 40 generated virtual case studies, which comprises of breast (113 cc), liver (220 cc) and lung (270 cc) metastases. FIG. 14 shows the distribution of T cells for activation in breast, liver and lung, respectively, for different values of parameters $h_a=[0,1]$ and $h_n/h_a=[0,1]$. Simulations reveal that the actual extravasation probability at the tissue of activation has a negligible influence on the systemic T cell distribution. However, the ratio of extravasation probabilities at non-activation sites versus activation sites, $h_n/h_a$, significantly determines activated T cell distribution regardless of activation site (FIG. 14). Intuitively, if $h_n/h_a=0$, T cell are unable to extravasate in any site other than tissue of activation, and no systemic response is possible. On the other hand, if extravasation occurs at all sites at equal strength (i.e., $h_n/h_a=1$), T cell distribution is identical regardless of tissue of activation. However, the T cells dissemination patterns vary greatly dependent on sites of activation for the intermediate $h_n/h_a$ values, including estimated $h_n/h_a=1/3$.

Figure 14B:
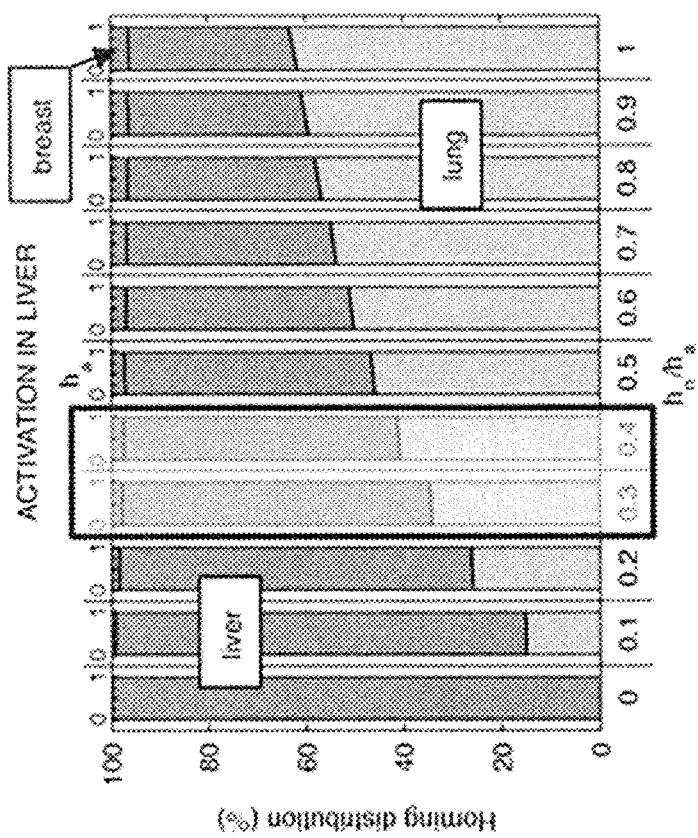
FIGS. 14A to 14C show T cells homing distribution for different activation sites and extravasation probabilities. Model predicted homing distributions between metastatic sites present in the first considered virtual case study comprised of breast (113 cc), liver (220 cc) and lung (270 cc) metastases for different sites of activation breast (FIG. 14A), liver (FIG. 14B), lung (FIG. 14C) and for different values of extravasation probabilities $h_n$, and $h_a$. Rectangles correspond to the narrow ranges around estimated value of $h_n/h_a$.
Figure 14A:
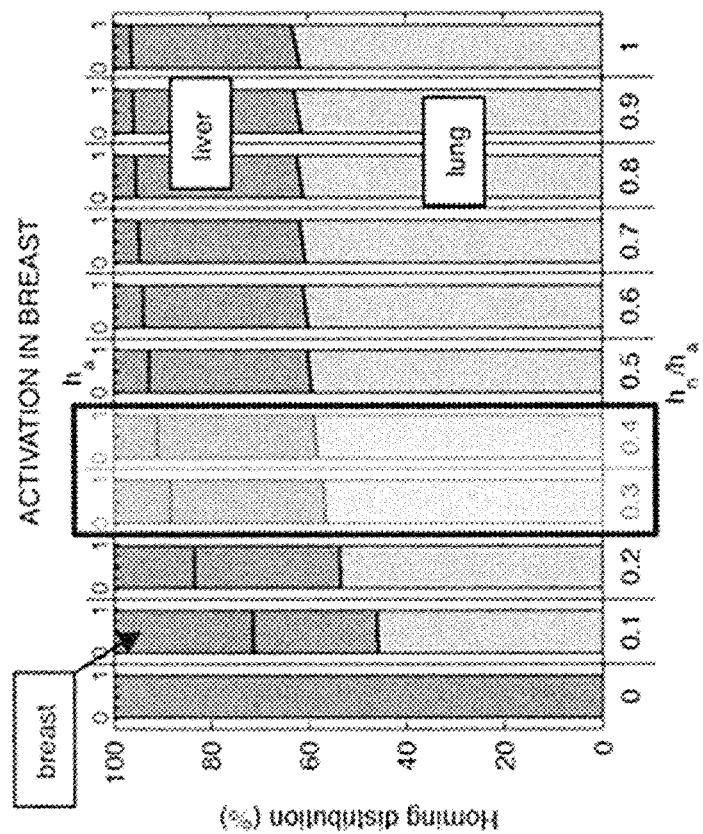
Figure 14D:
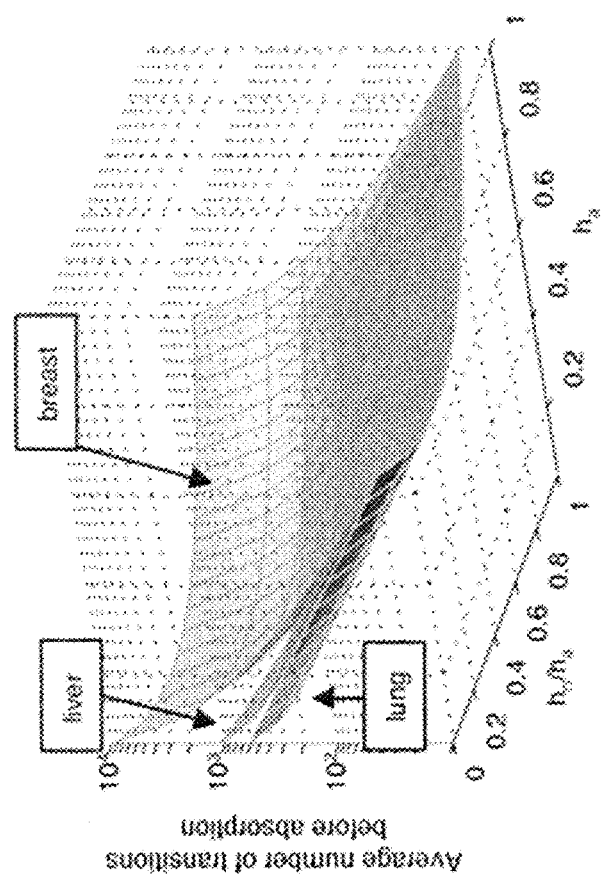
FIG. 14D shows the average number of transitions between model compartments before extravasation at one of the metastatic sites for different sites of activation and different extravasation probabilities $h_n$ and $h_a$. Calculations were performed using parameters reported in Table 2.
Figure 14C:
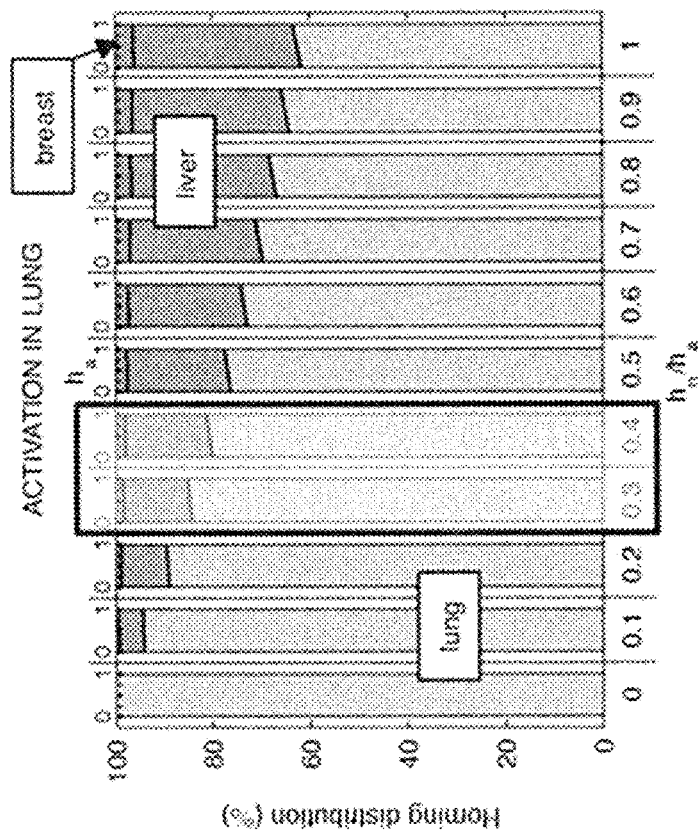

Given the complexity of the arterial tree, even flowing through specific site is a relatively rare event. In addition, both, T cell homing cue $h_a$ and its ratio to extravasation into distant tissue, $h_n/h_a$, significantly impact the number of circulatory cycles the T cells will traffic before extravasating at a tumor-harboring site (FIG. 14D). It follows from eqn. (C) that the average number of cycles can increase without any limits when one considers smaller and smaller values of parameter $h_a$. If $h_a=1$ and $h_n/h_a=1$, T cells will perform on average about 9 circulatory cycles with a blood recirculation time of 10 to 25 seconds (Puskas Z, et al. Der Radiologe. 1996 36(9):750-7), which translates to about 2 minutes. For lower values, $h_a=0.05$ and $h_n/h_a=0$, model suggests about 4500 circulatory cycles (up to about 32 hours) before certain extravasation in the case of T cell activation in the breast.

Figure 15A:
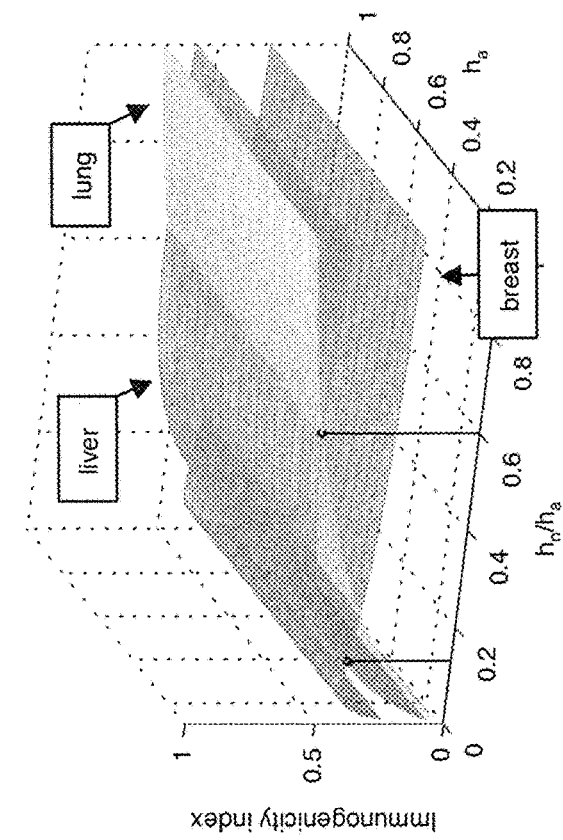
FIGS. 15A to 15B show comparison of normalized entropy values (FIG. 15A, eqn. (D)), and immunogenicity indices (FIG. 15B, eqn. (E)), between the metastatic sites present in the first considered case study comprised of breast (113 cc), liver (220 cc) and lung (270 cc) metastases for different extravasation probabilities $h_n$ and $h_a$.
Figure 15B:
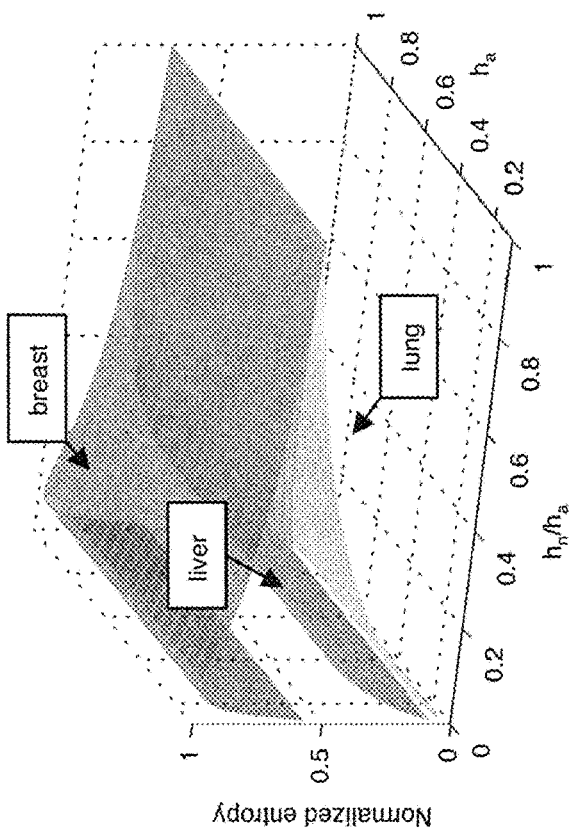

Entropy comparison between T cell homing distributions (eqn. (D)) shows that distribution of activated T cells closest to the uniform can be achieved after treating the breast tumor in this virtual patient example (FIG. 15A), regardless of extravasation probabilities $h_a$ and $h_n$. Targeting the lung tumor, however, yields a heavily skewed distribution among the metastatic sites, with lung being the largest attractor given the large BFF to the lung. To calculate the immunogenicity index (eqn. (E)), tumor sizes need to be integrated. In the virtual patient example, the liver metastases has the highest immunogenicity index for $h_n/h_a$ values between 15% and 60%, including the estimated value of $h_n/h_a=1/3$ (FIG. 15B).

Figure 15C:
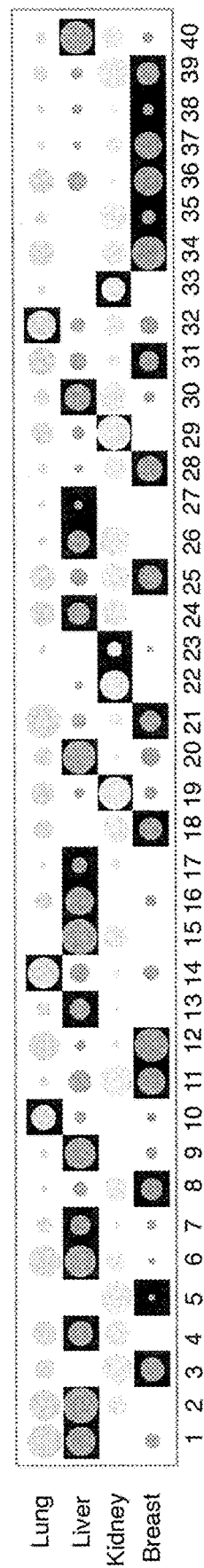
FIG. 15C shows results of the analysis of other 40 virtual case studies of possible metastatic tumors in lung, liver, kidney and the breast. Circles denote existence of the metastatic site and radius corresponds to the tumor size. Black background highlights the tumor with the highest immunogenicity index for $h_n/h_a=1/3$ and $h_a=0.6$. Calculations were performed using parameters reported in Table 2.

Sites having the highest immunogenicity index were further calculated in other virtual case studies for the estimated values of $h_n/h_a=1/3$ and $h_a=0.6$ (FIG. 15C). In a given patient specific setting, the largest tumor size or the combination of existing metastases alone are not the predictive factors when one considers the probability of triggering the systemic response. Indeed, in the case study No. 5, the much smaller breast tumor (53 cc) had higher immunogenicity index than much larger kidney tumor (254 cc). Case studies 20 and 21 have the same combination of metastatic sites, but the tumors with the highest immunogenicity indices are at different locations. Therefore, there is a need to apply proposed framework for every individual case separately.

Discussion

Transition from local to metastatic disease severely diminishes patient prognosis. 10-15% of breast cancer patients, the second most common cancer diagnosed worldwide, will develop metastasis within 3 years of diagnosis (McGuire A, et al. Cancer Metastasis Rev. 2015 34(1):145-55). Tumors for which no systemic screening for early detection exists are often diagnosed with metastatic diseases (Ovaries, lung), further emphasizing the urgent need to develop novel approaches that provide systemic cancer control with limited toxicity. Immunotherapy has been shown to synergize with local radiation (Reits E A, et al. J Exp Med. 2006 203(5):1259-71; Lugade A A, et al. J Immunol. 2005 174(12):7516-23; Vatner R E, et al. Front Oncol. 2014 4:325), which is currently explored in more than 10 active clinical trials (Vatner R E, et al. Front Oncol. 2014 4:325). However, understanding of the biological and physical principles underlying the complex dynamic interplay of radiation and immunotherapy, locally and especially systemically, is still in its infancy. Of fascinating interest are increasing case reports of abscopal responses of metastatic tumors distant to the areas targeted by radiation (Antoniades J, et al. Int J Radiat Oncol Biol Phys. 1977 2(1-2):141-7; Wersall P J, et al. Acta Oncol. 2006 45(4):493-7; Ehlers G, et al. Br J Radiol. 1973 46(543):220-2). Experiments were conducted to identify if different metastatic sites have different potentials to induce a systemic response, and if mathematical modeling can be used to identify the most promising treatment targets, either alone or in combination, on a per patient basis.

A systemic tumor-immune system interaction framework is proposed, which accounts for activated T cell trafficking through the host circulatory system. From the patient-specific distribution of the metastatic sites, which can be acquired from routinely taken PET/CT scans, combined with physiological information about T cell trafficking, the distribution of radiotherapy-facilitated activation of T cells for each metastatic site, either alone or in combination, can be estimated. Using a virtual patient cohort the activated T cell distribution was dependent on (i) the geographic distribution of metastatic sites, (ii) the tumor volume of each metastasis, and (iii) the site of activation. Integrating those patient-specific characteristics, the immunogenicity index can be calculated, which can support the clinical decision as to which metastatic site serves as the most promising local treatment target to induce abscopal responses. Disclosed is a process to quantify how local tumor-immune interactions may propagate systemically and predict patient-specific treatment targets to trigger abscopal effects.

Example 2

Systemic Interdependence of Metastatic Tumor Growth Through Activated T Cell Trafficking For illustration purpose the established Kuznetsov model of local tumor-immune interactions was used with reported parameter values (Kuznetsov V A, et al. Math Comput Model. 2001 33(12-13):1275-87). This module of the framework, however, is interchangeable for any tumor growth and immune modulation model (Example 3). In some embodiments, the model may be calibrated with organ-specific tumor growth kinetics and immune surveillance to fully integrate local and systemic dynamics and confidently support personalized decision making in the clinic.

Figure 16B:
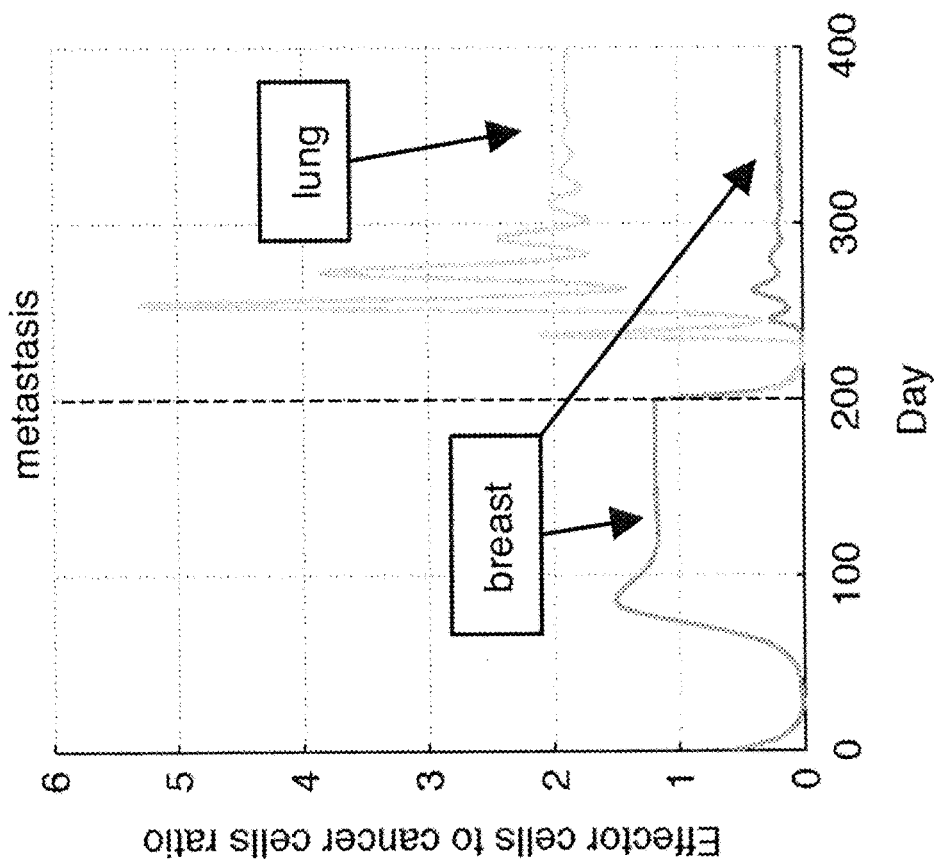
FIGS. 16A to 16B show model predicted growth of the primary breast tumor before and after onset of lung metastasis (FIG. 16A) together with corresponding number of infiltrating T cells (FIG. 16B).
Figure 16A:
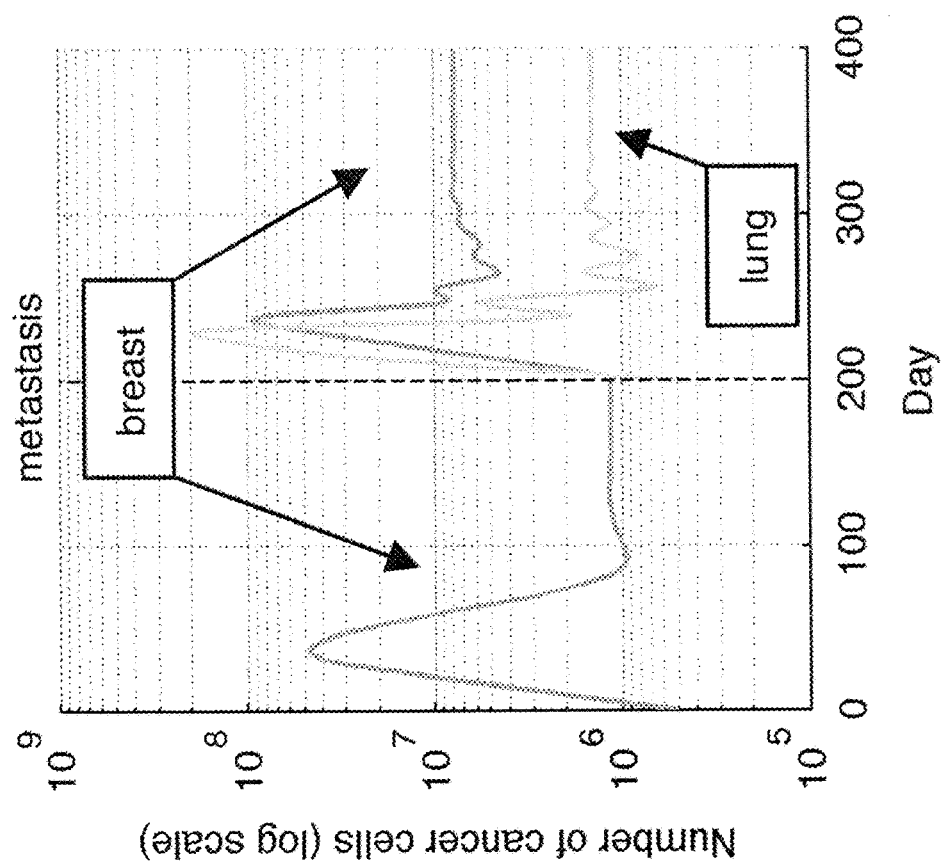
Figure 16D:
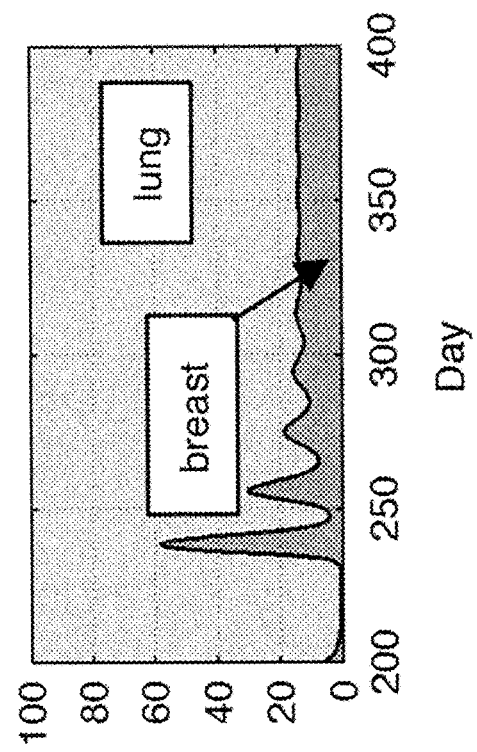
FIGS. 16C and 16D show dynamics patterns of T cells homing probabilities when T cells are activated in response to the breast tumor (FIG. 16C) and lung metastasis (FIG. 16D). Simulations were performed with $h_a=0.6$, $h_n=0.2$, and parameters reported in Tables 1 and 2, under additional assumption that the lung tumor has twice the nominal growth rate.
Figure 16C:
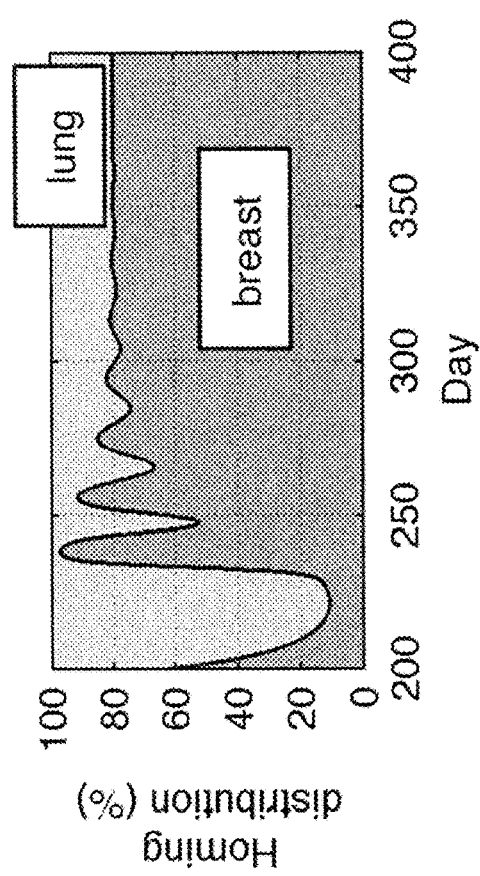
Figure 17B:
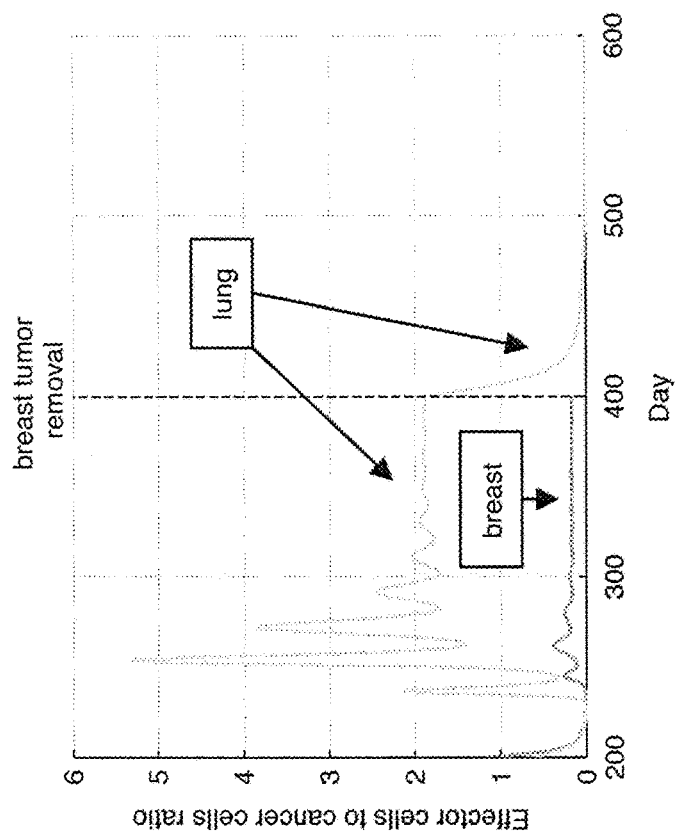
FIGS. 17A and 17B show that model predicted dynamics of the number of cancer cells (FIG. 17A) and effector to cancer cells ratio (FIG. 17B) in lung metastasis after surgical removal of the breast tumor and local effector cells at day 400. Simulations were performed with $h_a=0.6$, $h_n=0.2$, and parameters reported in Tables 1 and 2, under additional assumption that the lung tumor has twice the nominal growth rate.
Figure 17A:
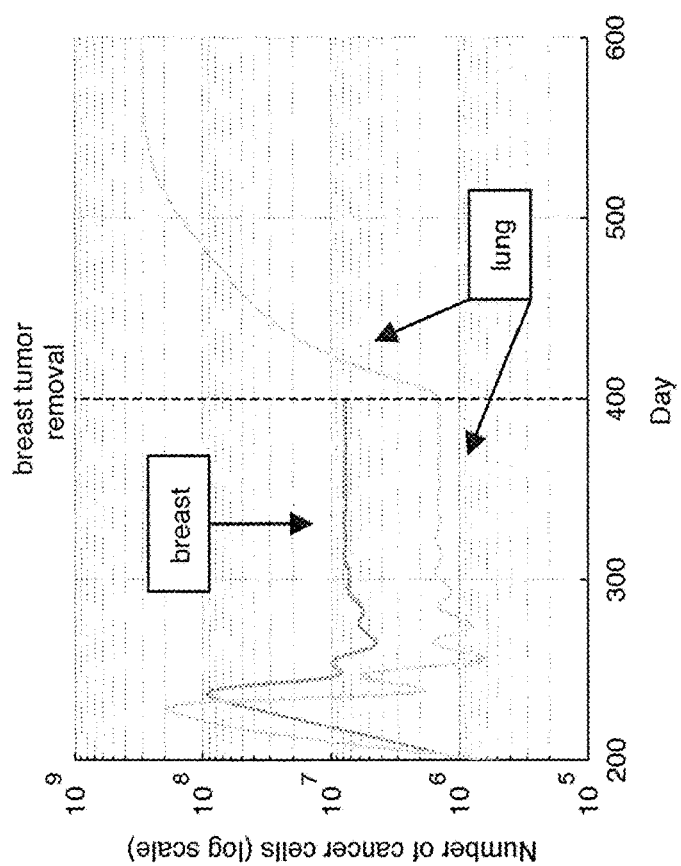

Simulation of primary tumor growth for 200 days show that a primary tumor can be modulated by cytotoxic immune surveillance, keeping the tumor in a dormant state significantly below the imposed carrying capacity (FIG. 16A). The onset of metastatic site disrupts the dynamic equilibrium between T cells and cancer cells in the primary site. Before the immune response against the metastasis is established locally, some of the T cells that are generated in the primary breast tumor traffic and extravasate at the metastatic site, allowing for a transient escape and progression of the primary tumor (FIG. 16B). After T cells activated by the lung metastasis begin trafficking in the circulatory system, the total number of T cell increases and an increase in T cells surveilling the breast cancer can be observed. However, because of the attained equilibrium of homing distributions (FIGS. 16C and 16D), the lower proportion of T cell penetrating the breast allows the tumor to attain dormancy with cell numbers significantly larger than pre-metastasis formation. Interestingly, the lung metastasis is also kept at a dormant state despite its larger growth rate, mostly due T cells that were generated in the breast and trafficked to the lung. What is most interesting, because of the large proliferation rate, lung tumor seeded alone would escape the immune surveillance and grow to imposed carrying capacity value (simulations not shown). Thus, surgical removal of the breast cancer, accompanied by removal of locally infiltrated T cells as well as prevention of future T cells activated in the breast, leads to a rapid progression of the lung metastasis and a substantial decrease of effector to cancer cells ratio in the lung (FIG. 17).

Example 3

Local Mathematical Model of Tumor-Immune Interactions

Figures 5, 6A:
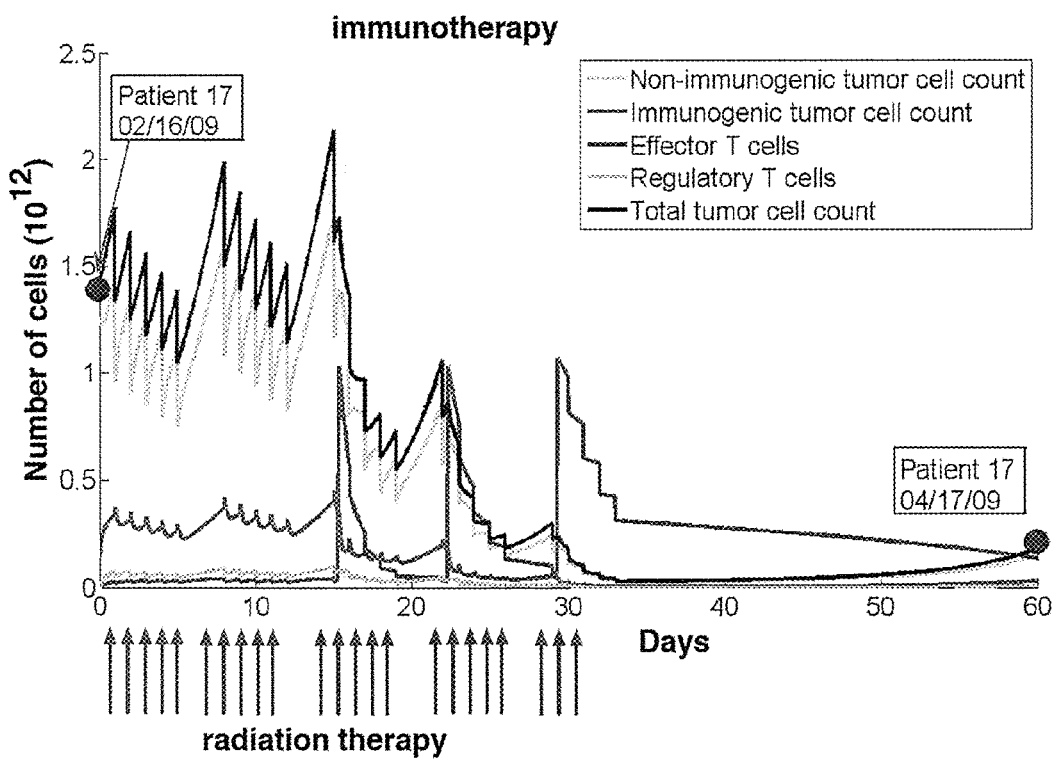
FIG. 5 is a proposed mathematical model of the interplay between Tumor (TN+TI) and Immune (R+E) populations and perturbation during radiation and immunotherapy.
FIGS. 6A to 6C show simulation results reproducing clinical tumor growth and T cell dynamics of responders (FIG. 6A, 6C) and nonresponders (FIG. 6B). The patient in FIG. 6C was a non-responder that became a responder with modified immunotherapy schedule.
Figure 6B:
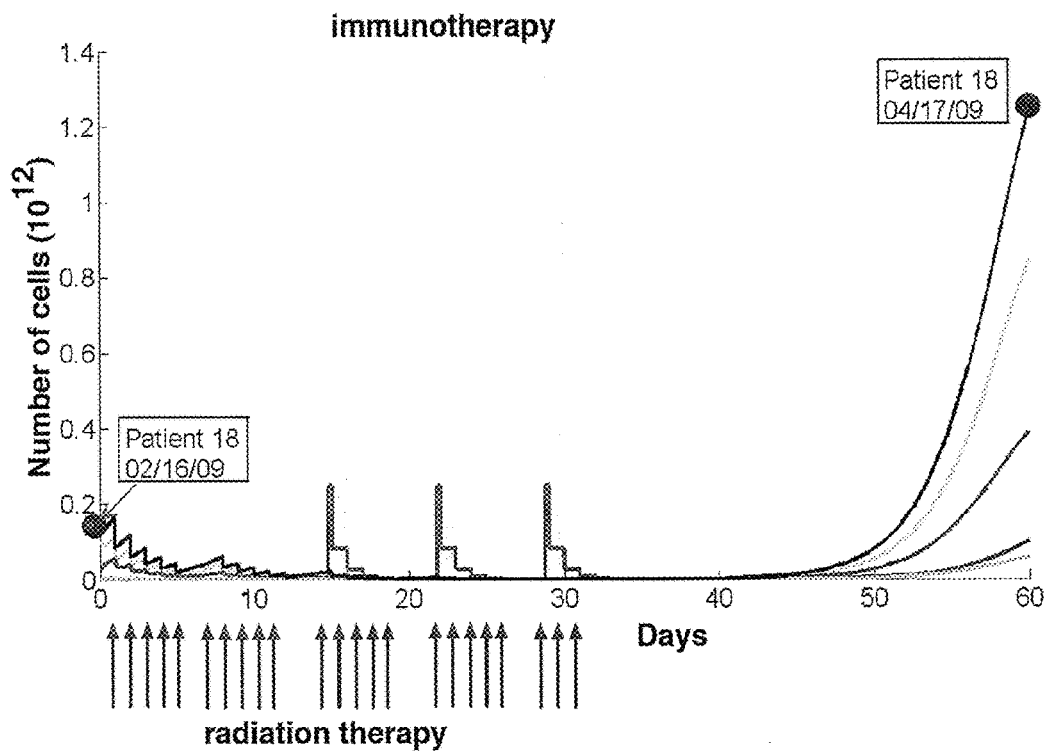
Figure 6C:
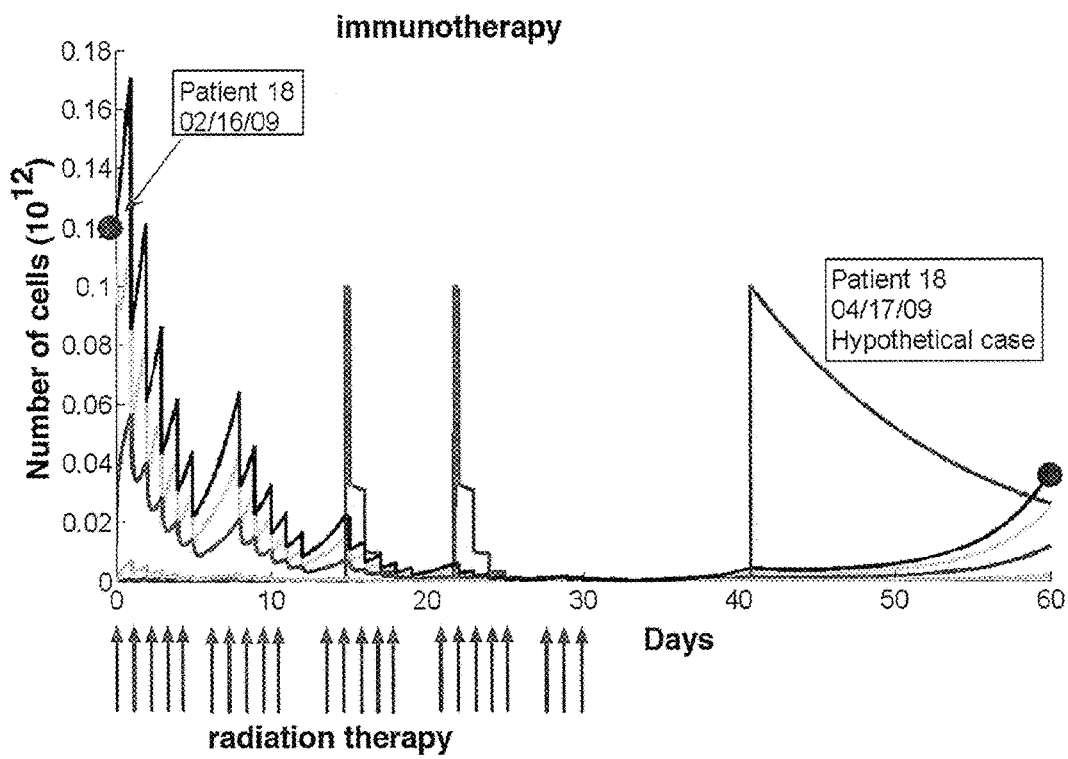

In some embodiments, a model of local tumor-immune interactions can be integrated into the framework. Cell populations of both primary and metastatic nodules exhibit heterogeneous immunogenicity [Tufail S, et al. Front Immunol. 4:254, 2013; Marte B. Nature. 501(7467):327, 2013]. Stimulation of immune effector cells is counterbalanced by tumor-mediated recruitment of immunoregulators [Ye J, et al. Cancer Res. 73(20):6137-48, 2013]. Immunotherapeutic injection of autologous dendritic cells transiently shifts the local immune profile in favor of effector cells [Ward S T, et al. The Lancet. 381:S113, 2013]. Local irradiation has been observed to induce a pro-inflammatory immune response as well as to shift non-immunogenic populations into an immunogenic phenotype in animal experiments [Demaria S, et al. Clin Cancer Res. 11(2 Pt 1):728-34, 2005] and exploratory clinical trials [Hiniker S M, et al. N Engl J Med. 366(21):2035-6, 2012]. For simplicity it is assumed that the tumor population is divided into immunogenic ($T_I$) and non-immunogenic ($T_N$) cells, and the immune system into Effector (E) and Regulatory (R) cells. These complex local dynamics can be converted in a differential equation model (FIG. 5). While the dynamics of this system are universal, transition rates and parameters are patient-specific. 17 patients (stage 2 soft-tissue sarcoma without metastatic spread) were enrolled in a Moffitt clinical trial that combined intratumoral administration of dendritic cells and local fractionated external beam radiation to determine localized radiation-immune system synergy [Finkelstein S E, et al. Immunotherapy. 4(4):373-382, 2012]. Preliminary results indicate that the mathematical model (FIG. 5) can reproduce tumor volume, T cell dynamics and treatment outcome for a responder and a non-responder from this patient cohort (FIG. 6).

To validate the model and derive statistically optimized parameter calibrations, patient data from all 17 patients in that clinical trial [Finkelstein S E, et al. Immunotherapy. 4(4):373-382, 2012] are evaluated. To achieve this, a genetic algorithm is deployed to fit the model to the available sequential measurements of tumor volume and CD3, CD 4 and CD8 counts for each patient. Genetic algorithms are established to explore large parameter spaces and compare simulation results to desired outcomes. The genetic algorithm is initialized with a population (n=1000) of random parameter values for the mathematical model. Parameter combinations that yield the smallest deviation from the clinical data forms the input population for the next iteration of simulations ('genetic selection'), complemented by random combinations of those successful parameter sets ('crossover') and random alterations in single parameter values ('mutations'). Through many iterations of this simulation-selection-modulation approach, parameter combinations that best describe patient response forms a 'virtual patient cohort'.

Example 4

Whole Body Personalized Metastatic-Lymphatic Interconnected Network Model

Figure 3:
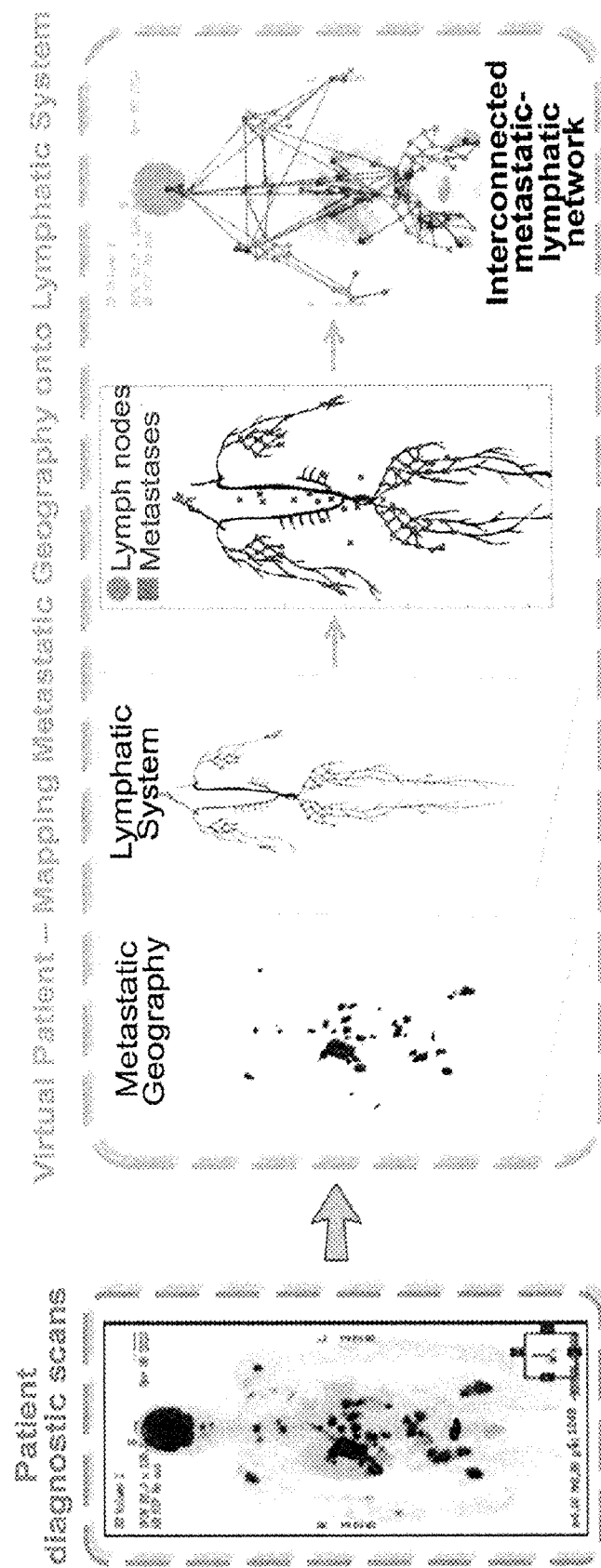
FIG. 3 shows the translation of radiological diagnostic scans into a 'virtual patient' interconnected metastatic-lymphatic network.

Diagnostic positron emission tomography (PET) scans or computer tomography thorax, abdomen, pelvis (CT TAP) scans are available for patients. Theses scans are used to accurately register the geographic location of each tumor site and their distance to the host lymphatic system. Three-dimensional radiological data sets are volume rendered and registered using scientific visualization software (Matlab, IDL, ImageJ) and image processing algorithms. The patient-specific geographic metastatic disease distribution is mapped onto a virtual lymphatic network to create a 'virtual patient' (FIG. 3). Lymphatic network interconnectivity with different metastatic sites is estimated from T cell infiltration immune scores (CD3, CD8) [Galon J, et al. J Transl Med. 10:1, 2012] through immunohistochemistry on 80 primary and metastatic frozen tumor samples from 20 patients in the Moffitt Cancer Center Total Cancer Care multidimensional data warehouse. Immune score is correlated with relative distance to lymph nodes to interconnect tumor sites with the lymphatic network.

Figure 4:
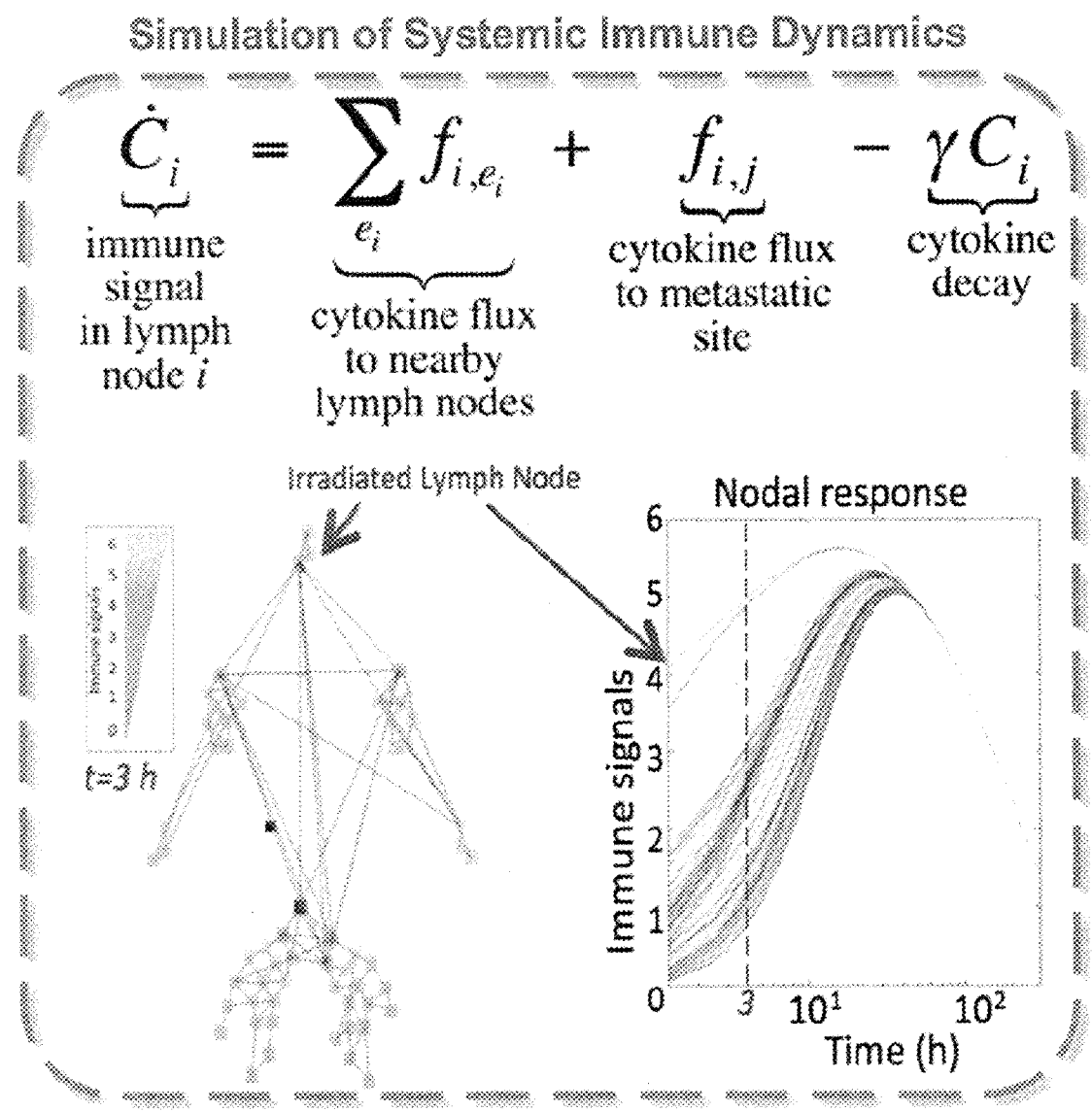
FIG. 4 shows spatio-temporal propagation of immune signals from single irradiated lymph nodes.

Central to the radiation and immune system orchestrated abscopal effect are immune signals that flow through the lymphatic network. Immune signals in each lymph node flow to adjacent lymph nodes as well as to nearby metastatic sites. The immune signal in each node can additionally be modulated by local irradiation that initiates an ad hoc immune response [Sharma A, et al. Clin Cancer Res. 19(17):4843-53, 2013]. A quantitative model was derived to capture these multiscale lymphatic network dynamics. The mathematical model allows tracking the spread of immune signals through the lymphatic network as a function of time and estimation of the global impact triggered by local perturbations. Preliminary simulations of immune signal propagation through the lymphatic network after local irradiation suggest a variable connectivity of lymph nodes and thus variable systemic impact (FIG. 4). Serial complete blood count data after local dendritic cell injection available from a clinical trial [Finkelstein S E, et al. Immunotherapy. 4(4):373-382, 2012] are used to calibrate and validate the model.

Example 5

Integrate Local and Systemic Models and Validate With Clinical Outcome

Figure 7:
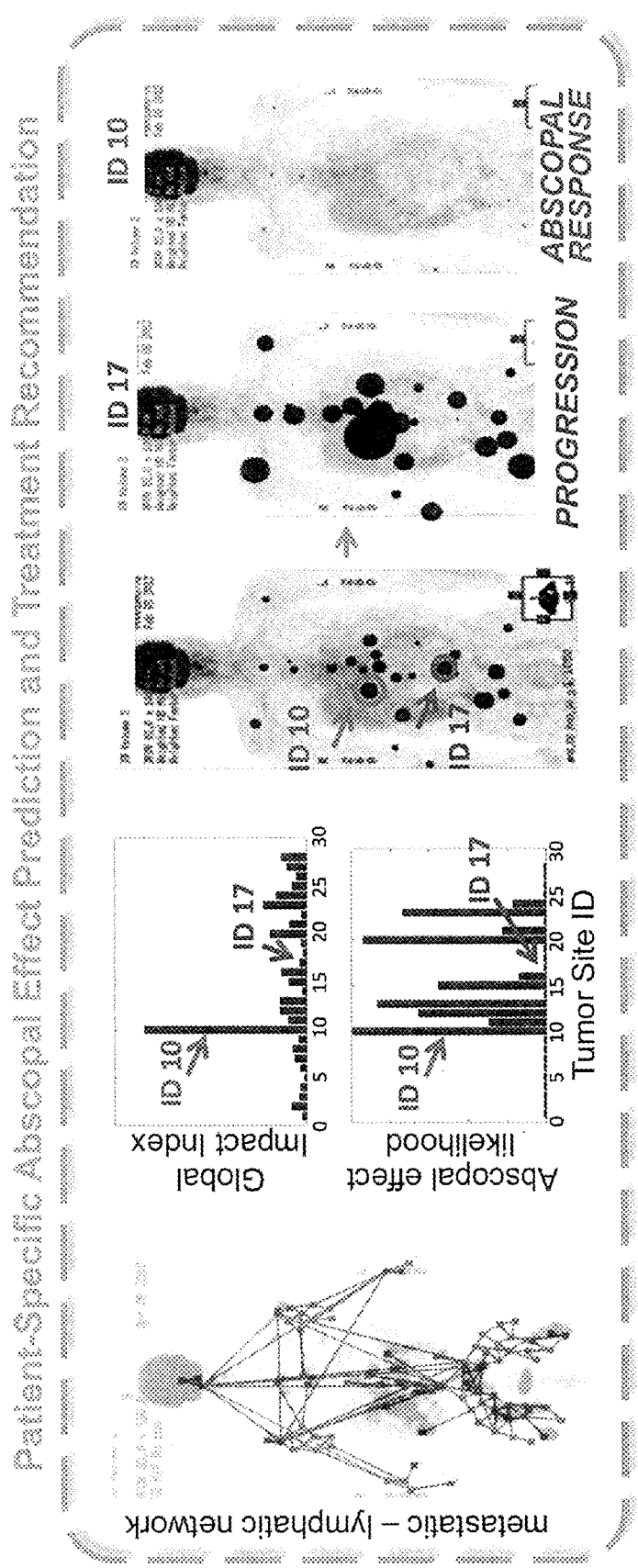
FIG. 7 provides framework results. Shown on the left is a patient-specific interconnected metastatic-lymphatic network. Metastases (blue) and lymph nodes (red) connected through the shortest paths. Shown center is the deviation of the global impact each tumor side has on the entire lymphatic network, and the likelihood of achieving an abscopal effect dependent on irradiated tumor site. Shown on the right are simulation results of patient-specific treatment. Abscopal effect achieved by irradiating tumor site ID 10 as observed clinically. Irradiation of tumor side ID 17 with little global impact yields local control but systemic progression.
Figure 8:
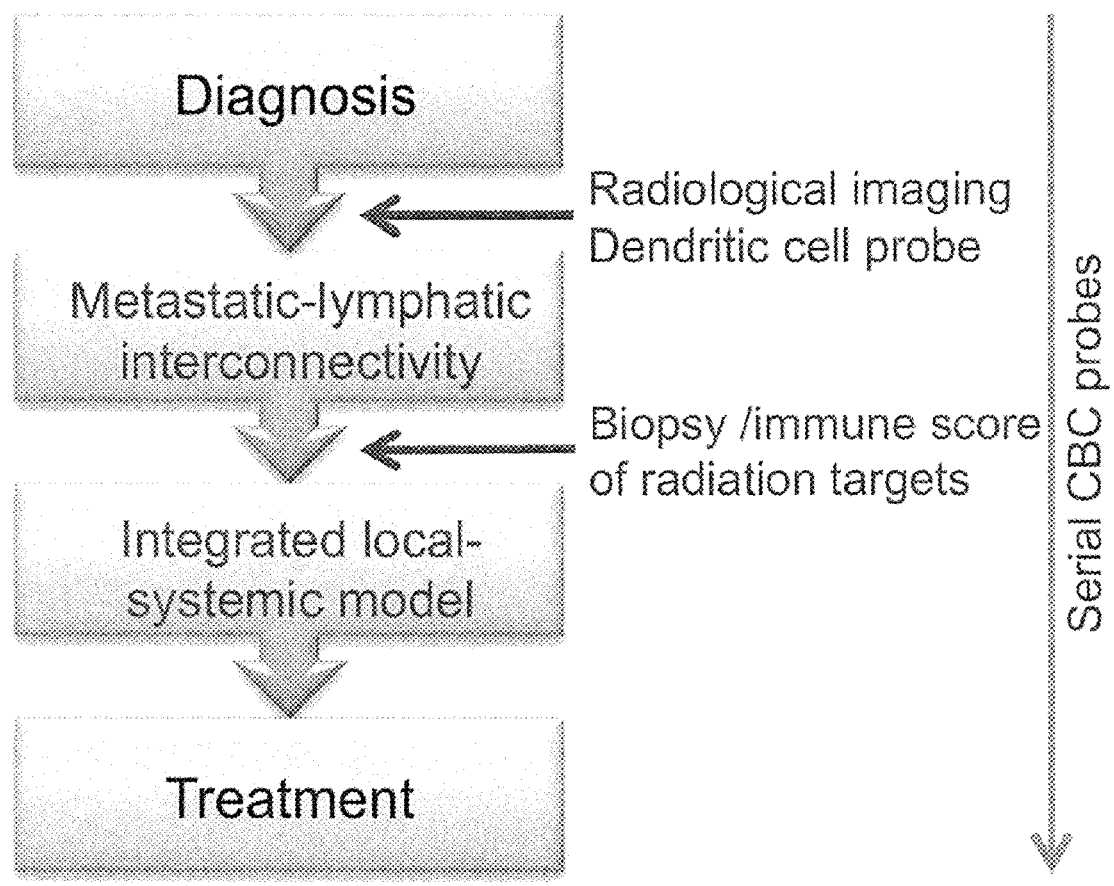
FIG. 8 is a diagram showing integration of the quantitative framework into the clinical protocol and high-resolution spatio-temporal cancer immunological data acquisition.
Figure 10A:
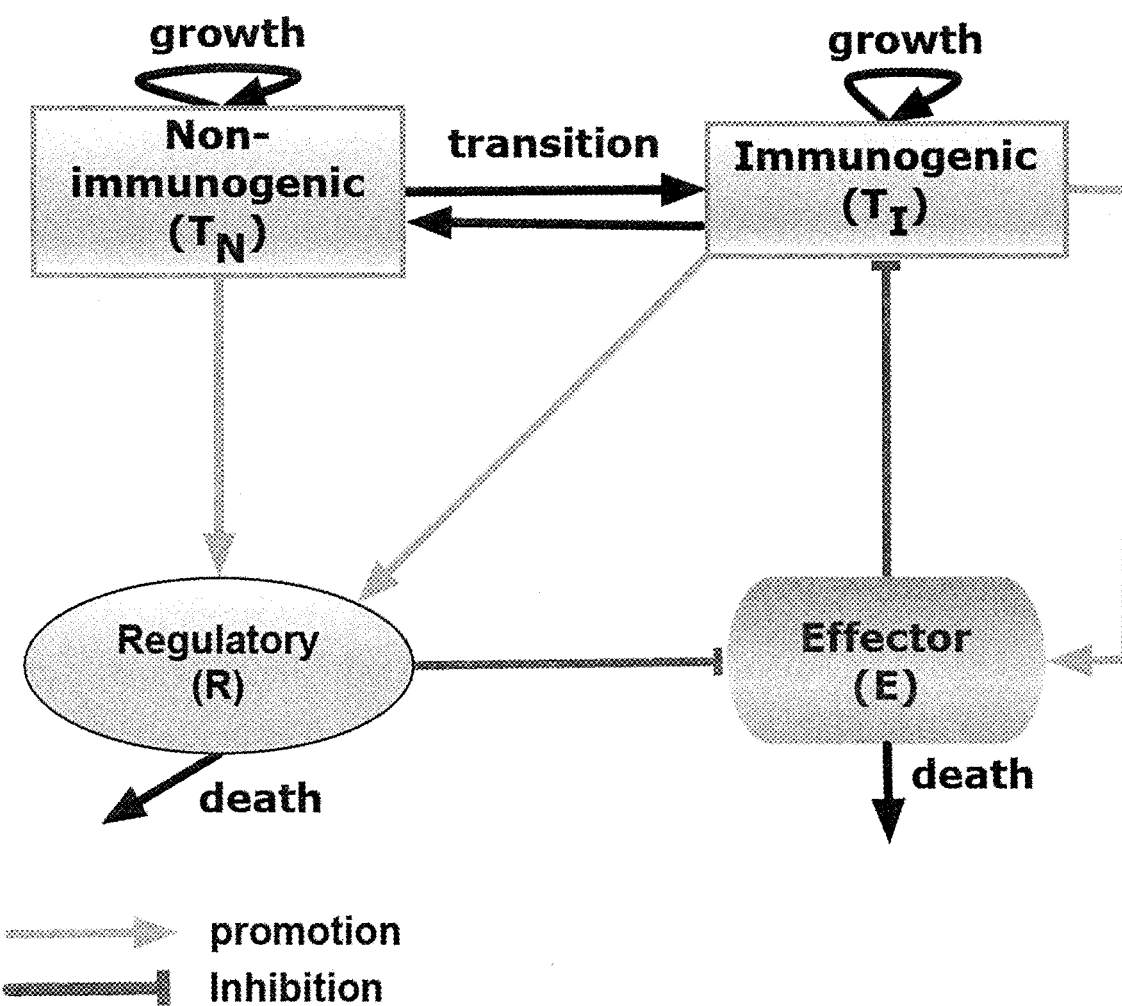
FIGS. 10A to 10C are schematics of the interplay between tumor and immune populations without treatment (FIG. 10A), with radiation therapy (FIG. 10B), and with immunotherapy (FIG. 10C).
Figure 10B:
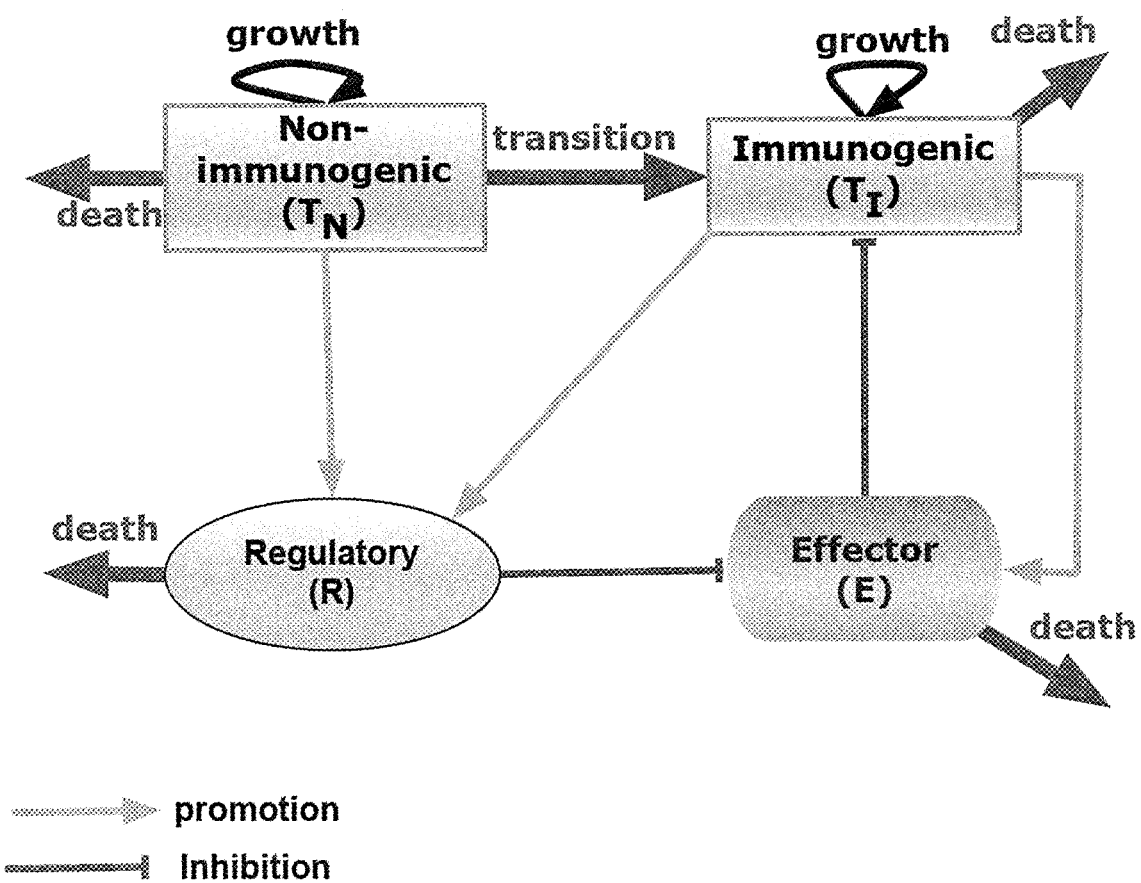
Figure 10C:
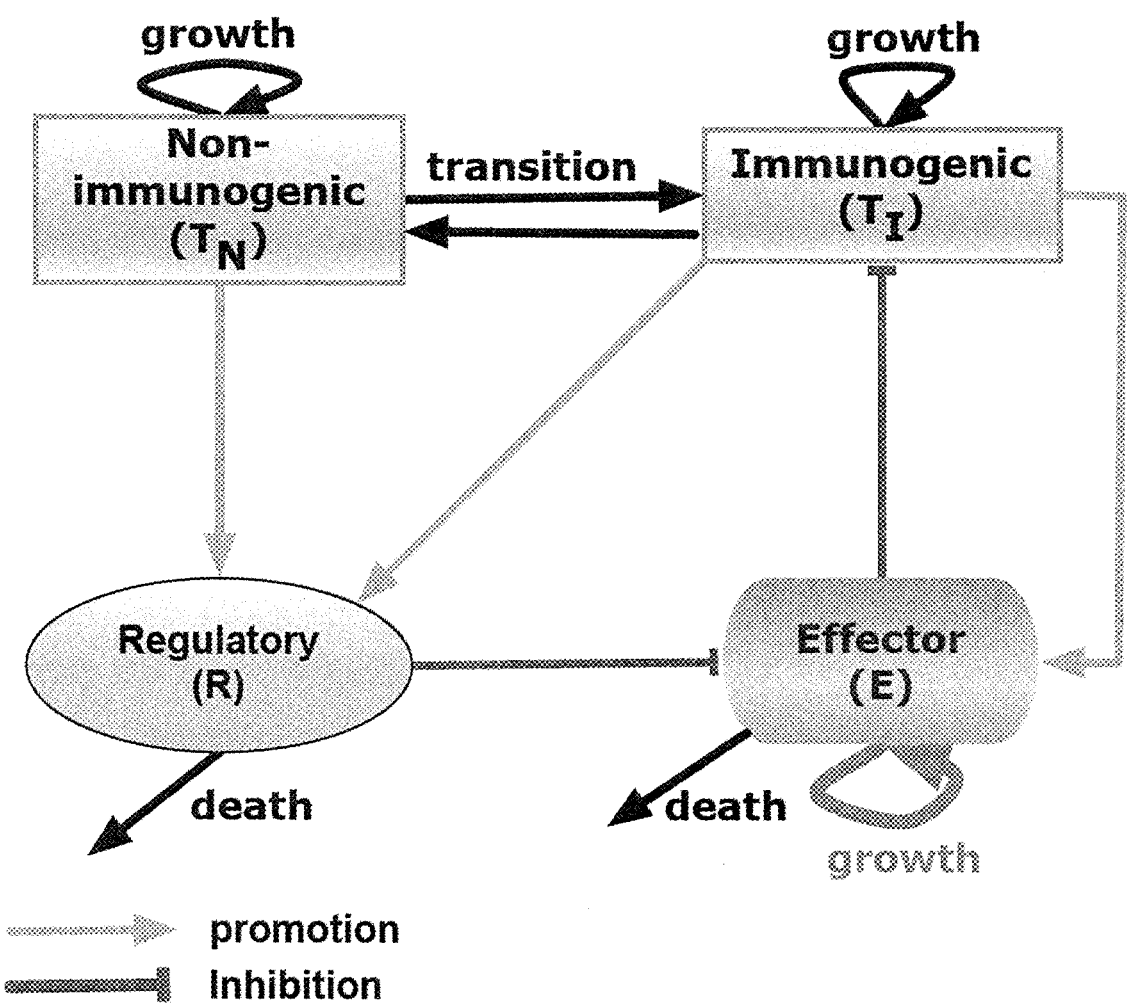
Figure 12:
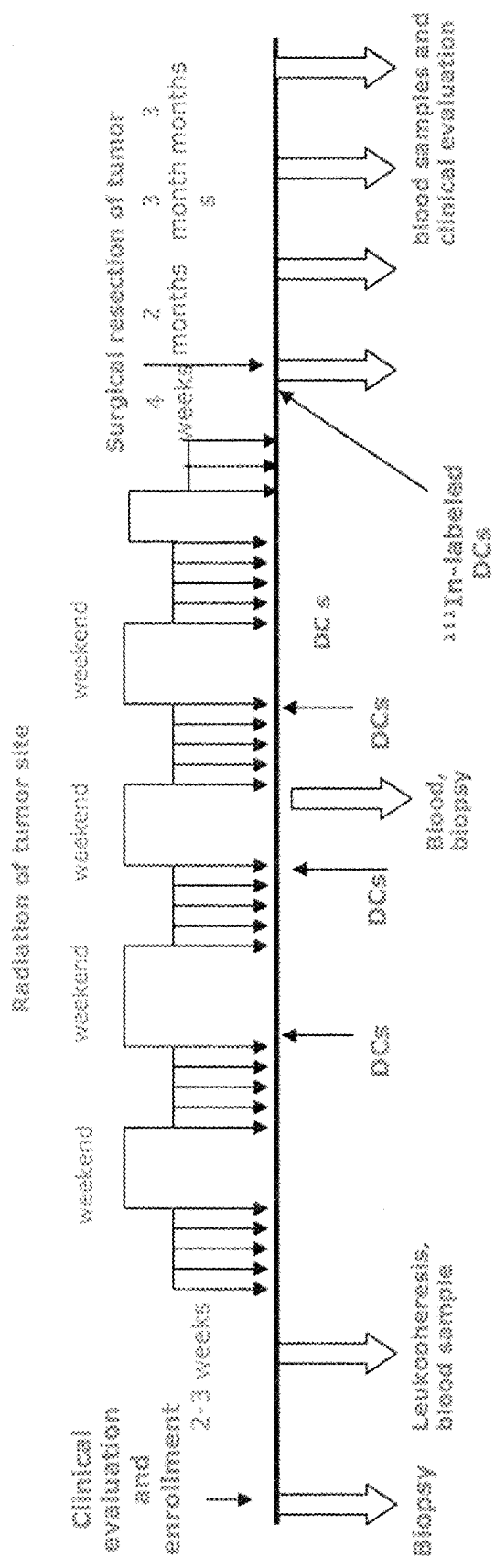
FIG. 12 is a diagram a representative protocol.

The local interaction model is combined with the whole body model to simulate patient specific systemic response to local irradiation and immunotherapy. Every cancerous lesion (primary tumor and metastatic nodules) dynamically interacts with a local immune system (Example 2; FIG. 5), and all lesions are interconnected through systemic communication (Example 1; FIG. 4). Each tumor experiences and corresponds to local as well as global signals. Results of local interactions are communicated through the metastatic-lymphatic network and influence subsequent dynamics of all other metastases dependent on their respective connectivities. Local radiotherapy is simulated independently on each metastatic nodule and transiently induced local immune response and systemic immune signal propagation is monitored. This gives a global impact index for each tumor side. Combined with observations of immune response in distant metastases and subsequent tumor modulation, the model yields the abscopal effect likelihood for irradiation of each individual metastatic site (FIG. 7).

The 'virtual patient' framework successfully simulated the abscopal effect for n=1 patient [Seung S K, et al. Sci Transl Med. 4(137):137ra74, 2012]. For this patient, the model suggests that the tumor that received local irradiation in the clinic was the only lesion that could trigger such a response. Irradiation of each other lesion would have resulted in local tumor control but systemic disease progression (FIG. 7). This suggests that careful selection of immuno-communicative 'hub' nodes holds the key to successful abscopal disease control.

In a retrospective study of 20 patients, diagnostic PET or CT TAP scans are used to generate patient-specific interconnected metastatic-lymphatic network graphs. Immunohistochemistry on primary and metastatic tumor sites for each patient provide local immune infiltration immune scores and in combination with serial complete blood counts suggest systemic immune signal flow. The actual clinically applied treatments are simulated for that patient. Then using the available sequential radiological images that were obtained during the course of treatment (4-6 per annum per patient) personalized model predictions are calibrated and validated. Model predictions are compared to patient outcome, in terms of treatment responder or non-responder.

A nice feature of the disclosed integrated approach is that for the patients in the retrospective study that had progressive disease, it can investigate if an alternative local radiotherapy of single or combinations of metastatic nodes could have triggered abscopal effects. The focus of this 'virtual patient' treatment design framework is on abscopal effects in metastatic renal cell carcinoma in line with the clinical expertise of the investigator team. The translation of the developed modules to other metastatic diseases with reported abscopal effects like metastatic melanoma, hepatocellular carcinoma and chronic lymphocytic lymphoma [Wersäll P J, et al. Acta Oncol. 45(4):493-7, 2006; Postow M A, et al. N Engl J Med. 366(10):925-31, 2012; Ohba K, et al. Gut. 43(4):575-7, 1998] is straightforward and a natural extension of our work here, but would need to be implemented in collaboration with clinical experts in those cancers.

Computing Device

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 19:
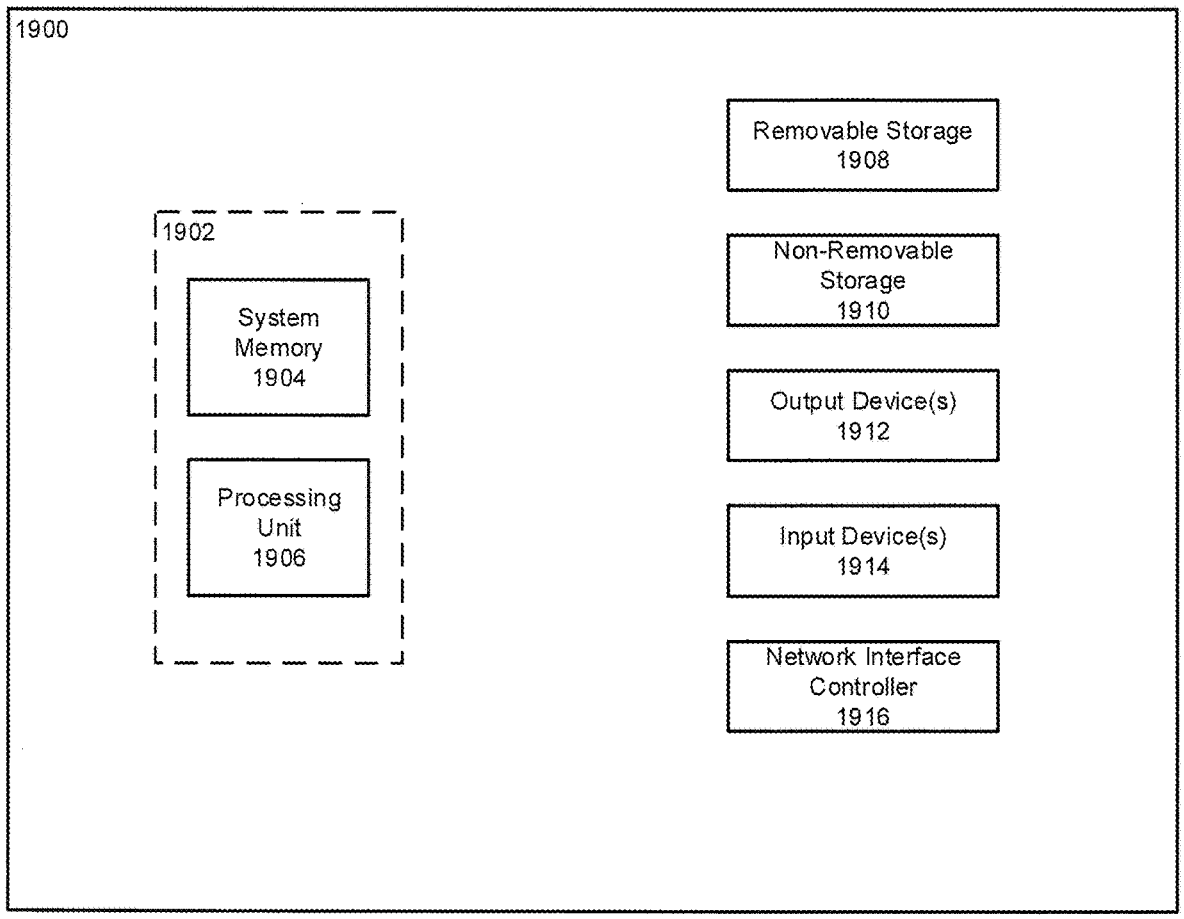
FIG. 19 is an example computing device that can be configured to perform operations described herein.

When the logical operations described herein are implemented in software, the process may execute on any type of computing architecture or platform. For example, referring to FIG. 19, an example computing device upon which embodiments of the invention may be implemented is illustrated. The computing device 1900 may include a bus or other communication mechanism for communicating information among various components of the computing device 1900. In its most basic configuration, computing device 1900 typically includes at least one processing unit 1906 and system memory 1904. Depending on the exact configuration and type of computing device, system memory 1904 may be volatile (such as random access memory (RAM)), non-volatile (such as read-only memory (ROM), flash memory, etc.), or some combination of the two. This most basic configuration is illustrated in FIG. 19 by dashed line 1902. The processing unit 1906 may be a standard programmable processor that performs arithmetic and logic operations necessary for operation of the computing device 1900.

Computing device 1900 may have additional features/functionality. For example, computing device 1900 may include additional storage such as removable storage 1908 and non-removable storage 1910 including, but not limited to, magnetic or optical disks or tapes. Computing device 1900 may also contain network connection(s) 1916 that allow the device to communicate with other devices. Computing device 1900 may also have input device(s) 1914 such as a keyboard, mouse, touch screen, etc. Output device(s) 1912 such as a display, speakers, printer, etc. may also be included. The additional devices may be connected to the bus in order to facilitate communication of data among the components of the computing device 1900. All these devices are well known in the art and need not be discussed at length here.

The processing unit 1906 may be configured to execute program code encoded in tangible, computer-readable media. Computer-readable media refers to any media that is capable of providing data that causes the computing device 1900 (i.e., a machine) to operate in a particular fashion. Various computer-readable media may be utilized to provide instructions to the processing unit 1906 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1906 may execute program code stored in the system memory 1904. For example, the bus may carry data to the system memory 1904, from which the processing unit 1906 receives and executes instructions. The data received by the system memory 1904 may optionally be stored on the removable storage 1908 or the non-removable storage 1910 before or after execution by the processing unit 1906.

Computing device 1900 typically includes a variety of computer-readable media. Computer-readable media can be any available media that can be accessed by device 1900 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 1904, removable storage 1908, and non-removable storage 1910 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1900. Any such computer storage media may be part of computing device 1900.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A system for providing a personalized treatment plan for a subject with a plurality of tumor lesions in two or more tumor bearing organs, comprising: a processor; and
    a memory operably coupled to the processor, the memory having computer-executable instructions stored thereon that, when executed by the processor, cause the processor to:
        receive the at least one radiological image of the subject;
        determine a respective volume of each of the tumor lesions using at least one radiological image of the subject;
        obtain a respective physiologic blood flow fraction associated with each of the tumor lesions;
        obtain a respective T cell extravasation probability associated with each of the tumor lesions;
        calculate a respective homing distribution for each of the tumor lesions based on the respective volume of each of the tumor lesions, the respective physiologic blood flow fraction associated with each of the tumor lesions, and the respective T cell extravasation probability associated with each of the tumor lesions; wherein calculating the respective homing distribution for each of the tumor lesions comprises calculating a respective infiltration probability for each of the tumor lesions that predicts whether a T cell in circulation will infiltrate each of the tumor lesions in a single circulatory cycle, and wherein the respective infiltration probability for each of the tumor lesions is based on the respective volume of each of the tumor lesions, the respective physiologic blood flow fraction associated with each of the tumor lesions, and the respective T cell extravasation probability associated with each of the tumor lesions;
        calculate a respective immunogenicity index value for each of the tumor lesions based on the respective volumes of each of the tumor lesions and the respective homing distributions for each of the tumor lesions; and
        provide a recommendation for treating one or more of the tumor bearing organs with a targeted therapy that induces immunogenic cell death based on the respective immunogenicity index values for each of the tumor lesions.

2. The system of claim 1, wherein the at least one radiological image of the subject comprises positron emission tomography (PET) scans, x-ray computer tomography, or a combination thereof.

3. The system of claim 1, wherein the respective T cell extravasation probability comprises a probability of T cells activated in a tumor bearing organ of each of the tumor lesions, not activated in the tumor bearing organ of each of the tumor lesions, or a combination thereof.

4. The system of claim 1, wherein the memory has further computer-executable instructions stored thereon that, when executed by the processor, cause the processor to calculate a respective volume ratio of: (i) the respective volume of each of the tumor lesions to (ii) a volume of a tumor bearing organ of each of the tumor lesions, wherein the respective volume ratio for each of the tumor lesions is used in the calculation of the respective immunogenicity index value for each of the tumor lesions.

5. The system of claim 1, wherein the memory has further computer-executable instructions stored thereon that, when executed by the processor, cause the processor to calculate a respective blood flow fraction ratio of: (i) the respective physiologic blood flow fraction associated with each of the tumor lesions to (ii) a respective physiologic blood flow fraction associated with a compartment of each of the tumor lesions, wherein the respective blood flow fraction ratio for each of the tumor lesions is used in the calculation of the respective immunogenicity index value for each of the tumor lesions.

6. The system of claim 1, wherein the respective immunogenicity index values for each of the tumor lesions predicts the most likely target for local therapy that induces immunogenic cell death to induce an abscopal effect.

7. The system of claim 6, wherein the recommendation is to treat a tumor bearing organ with the largest immunogenicity index.

8. The system of claim 6, wherein the recommendation is to treat a plurality of tumor bearing organs with the combined highest immunogenicity index.

9. The system of claim 8, wherein the memory has further computer-executable instructions stored thereon that, when executed by the processor, cause the processor to consider a first preselected tumor bearing organ as a necessary target for treatment and provide a recommendation for irradiating a second tumor bearing organ having tumor lesions with the highest immunogenicity index in view of a preselected tumor bearing organ.

10. The system of claim 1, wherein calculating the respective homing distribution for each of the tumor lesions comprises calculating a respective homing probability for each of the tumor lesions that predicts the relative number of activated T cells that will home to each of the tumor lesions, and wherein the respective homing probability for each of the tumor lesions is based on the respective infiltration probability for each of the tumor lesions.

11. The system of claim 10, wherein calculating the respective homing distribution for each of the tumor lesions comprises calculating a respective homing distribution entropy value for each of the tumor lesions that predicts the relative distribution of T cells activated in each of the tumor lesions, and wherein the respective homing distribution entropy value for each of the tumor lesions is based on a total number of the tumor lesions and the respective homing probability for each of the tumor lesions.

12. The system of claim 11, wherein the respective immunogenicity index value for each of the tumor lesions is based on the respective homing distribution entropy value for each of the tumor lesions and the respective volume of each of the tumor lesions.

* * * * *